US010682324B2

(12) United States Patent
Abreo et al.

(10) Patent No.: US 10,682,324 B2
(45) Date of Patent: Jun. 16, 2020

(54) HEALING TOPICAL COMPOSITION

(71) Applicant: FLORENGALE, LLC, Jamul, CA (US)

(72) Inventors: Melwyn Abreo, Jamul, CA (US); Carol McBride, Jamul, CA (US); Talal Sheena, Jamul, CA (US)

(73) Assignee: FLORENGALE, LLC, Jamul, CA (US)

( * ) Notice: Subject to any disclaimer, the term of this patent is extended or adjusted under 35 U.S.C. 154(b) by 0 days.

(21) Appl. No.: 15/546,629

(22) PCT Filed: Jan. 27, 2016

(86) PCT No.: PCT/US2016/015135
§ 371 (c)(1),
(2) Date: Jul. 26, 2017

(87) PCT Pub. No.: WO2016/123223
PCT Pub. Date: Aug. 4, 2016

(65) Prior Publication Data
US 2018/0015060 A1 Jan. 18, 2018

Related U.S. Application Data

(60) Provisional application No. 62/108,492, filed on Jan. 27, 2015.

(51) Int. Cl.
*A61K 31/198* (2006.01)
*A61K 31/375* (2006.01)
*A61K 47/10* (2017.01)
*A61K 9/06* (2006.01)
*A61K 45/06* (2006.01)
*A61K 9/00* (2006.01)
*A61F 13/00* (2006.01)

(52) U.S. Cl.
CPC ...... *A61K 31/198* (2013.01); *A61F 13/00063* (2013.01); *A61K 9/0014* (2013.01); *A61K 9/06* (2013.01); *A61K 31/375* (2013.01); *A61K 45/06* (2013.01); *A61K 47/10* (2013.01); *A61K 2300/00* (2013.01); *A61K 2800/522* (2013.01)

(58) Field of Classification Search
CPC ...... A61K 31/198; A61K 9/0014; A61K 9/06; A61K 31/375; A61K 45/06; A61K 47/10; A61F 12/00063
USPC ...................................................... 514/562
See application file for complete search history.

(56) References Cited

U.S. PATENT DOCUMENTS

| 5,451,405 | A |   | 9/1995  | Zhang et al. |                       |
|-----------|---|---|---------|--------------|-----------------------|
| 5,691,380 | A | * | 11/1997 | Mason        | .......... A61K 8/447 |
|           |   |   |         |              | 424/401               |
| 5,906,811 | A | * | 5/1999  | Hersh        | .......... A61K 8/02  |
|           |   |   |         |              | 424/49                |
| 6,566,401 | B2 |  | 5/2003  | Herzenberg et al. | |
| 2004/0091506 | A1 | | 5/2004 | Bommarito | |
| 2010/0021399 | A1 | | 1/2010 | Rampoldi et al. | |
| 2011/0014285 | A1 | * | 1/2011 | Herzenberg | ......... A61K 9/0014 |
|   |   |   |   |   | 424/474 |
| 2012/0135062 | A1 | | 5/2012 | Nisbet | |
| 2014/0128470 | A1 | | 5/2014 | Pavliv | |
| 2017/0333393 | A1 | | 11/2017 | Salinas et al. | |

FOREIGN PATENT DOCUMENTS

| EP | 1 055 720 A2 | 11/2000 |
| EP | 1 055 720 A3 | 11/2000 |
| EP | 1 055 720 B1 | 11/2000 |
| EP | 2 397 125 A1 | 12/2011 |
| WO | WO-93/04669 A1 | 3/1993 |
| WO | WO-00/40217 A1 | 7/2000 |
| WO | WO-2006/116353 A2 | 11/2006 |
| WO | WO-2006/116353 A3 | 11/2006 |
| WO | WO-2013/138744 A1 | 9/2013 |

OTHER PUBLICATIONS

Al-Muhammed, J. et al. (May-Jun. 1996). "In-vivo studies on dexamethasone sodium phosphate liposomes," J Microencapsul 13(3):293-306.
Berge, S.M. et al. (Jan. 1977). "Pharmaceutical Salts," *Journal of Pharmaceutical Science* 66:1-19.
Chonn, A. et al. (Dec. 1995). "Recent advances in liposomal drug-delivery systems," *Curr Opin Biotechnol* 6(6):698-708.
Extended European Search Report dated Aug. 28, 2018, for EP Patent Application No. 16744036.1, 8 pages.
Eyles, J.E. et al. (Jul. 1997). "Oral delivery and fate of poly(lactic acid) microsphere-encapsulated interferon in rats," J. Pharm. Pharmacol. 49(7):669-674.
Gao, Z.H. et al. (Jun. 1995). "Controlled release of a contraceptive steroid from biodegradable and injectable gel formulations: in vitro evaluation," Pharm. Res 12(6):857-863.
International Search Report dated Apr. 14, 2016, for PCT Application No. PCT/US2016/015135, filed Jan. 27, 2016, 3 pages.
Ostro, M.J. et al. (Aug. 1989). "Use of liposomes as injectable-drug delivery systems," *Am J Hosp Pharm* 46(8):1576-1587.
Rao. K.P. (1995). "Recent developments of collagen-based materials for medical applications and drug delivery systems," *J. Biomater Sci. Polym. Ed.* 7(7):623-645.
Written Opinion dated Apr. 14, 2016, for PCT Application No. PCT/US2016/015135, filed Jan. 27, 2016, 5 pages.

* cited by examiner

*Primary Examiner* — Yevgeny Valenrod
(74) *Attorney, Agent, or Firm* — Edward D. Grieff; Mintz, Levin, Cohn, Ferris, Glovsky and Popeo, P.C.

(57) ABSTRACT

There are provided, inter alia, novel stabilized compositions for treating skin conditions wherein a therapeutically effective dosage of sulfur compound is applied which results in healing. The utilized dosage of sulfur compound results in a quicker breakdown of the virus capsid structure, resulting e.g., in faster healing. The dosing regimen to maintain the concentrations of the sulfur containing amino acid at the affected site also helps achieve quicker healing. The formulations and the methods are applicable to a variety of skin conditions including cold sores, herpes, genital herpes and shingles.

36 Claims, No Drawings

HEALING TOPICAL COMPOSITION

CROSS-REFERENCES TO RELATED APPLICATIONS

This application is a § 371 US national phase of International Application No. PCT/US2016/15135 filed Jan. 27, 2016, and claims the benefit of U.S. Provisional Application No. 62/108,492, filed Jan. 27, 2015, the entire contents of which are incorporated herein by reference in their entireties and for all purposes.

BACKGROUND OF THE INVENTION

Herpesviridae is a family of DNA viruses that cause diseases in animals, including humans and is also commonly referred to as herpesviruses. Common species of Herpesviridae, include HSV-1 and HSV-2 (both of which can cause orolabial herpes and genital herpes), *Varicella zoster* virus (which causes chicken-pox and shingles), Epstein-Barr virus (which causes mononucleosis), and Cytomegalovirus. Herpesviruses are widespread among humans. More than 90% of adults have been infected with at least one Herpesvirus, and a latent form of the virus remains in most people. There are 8 herpesvirus types that infect humans: herpes simplex viruses 1 and 2, varicella-zoster virus, EBV (Epstein-Barr virus), human cytomegalovirus, human herpesvirus 6, human herpesvirus 7, and Kaposi's sarcoma-associated herpesvirus. There are more than 130 herpesviruses, and some are from mammals, birds, fish, reptiles, amphibians, and molluscs.

Herpes simplex infections are categorized based on the part of the body infected. Oral herpes involves the face or mouth and may result in small blisters in groups sometimes referred to as cold sores or fever blisters. There are two types of herpes simplex virus, type 1 (HSV-1) and type 2 (HSV-2). HSV-1 causes oral infections and may be transmitted by direct contact with body fluids or lesions of an infected individual. Worldwide rates of HSV-1 or HSV-2 are between 60% and 95% in adults.

Thus, there is a need in the art for effective treatments of herpesvirus. Provided here are solutions to these and other problems in the art.

BRIEF SUMMARY OF THE INVENTION

This application relates, inter alia, to the treatment of skin conditions such as viral, bacterial, fungal and other inflammatory skin conditions occurring in humans and animals or mammals and provides stable useful topical formulations, dosage forms and dosing regimens improvably effective for arresting and treating such skin outbreaks, especially those caused by hCMV, HSV1, HSV2, infections including genital herpes, shingles (herpes zoster), chicken pox and warts (HPV). The skin, eye, ear, nose, mouth and mucosal applications can be targeted with these formulations.

In a first aspect, there is provided a pharmaceutical composition including a pharmaceutical acceptable carrier, an N-acetylcysteine or derivative thereof and an antioxidant compound.

In another aspect, there is provided a pharmaceutical formulation including an N-acetylcysteine or derivative thereof.

In another aspect, there is provided a dermal patch including an N-acetylcysteine or derivative thereof and an amount of an antioxidant compound sufficient to reduce oxidation of the N-acetylcysteine or derivative thereof relative to the absence of the antioxidant.

In another aspect, there is provided a method of treating a herpesvirus infection in a subject. The method includes administering an effective amount of the pharmaceutical composition or a dermal patch as disclosed herein.

In another aspect, there is provided a method for preparing a pharmaceutical composition. The method includes mixing an N-acetylcysteine or derivative thereof with a liquid pharmaceutical carrier within a container, wherein the liquid pharmaceutical carrier is anhydrous and substantially free of oxygen gas.

DETAILED DESCRIPTION OF THE INVENTION

Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present compounds. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —$CO_2$R', —CONR'R", —OC(O)N R'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", NR'C=(O)NR"NR'''R"", —CN, —$NO_2$, in a number ranging from zero to (2m'+1), where m' is the total number of carbon atoms in such radical. R, R', R", R''', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound disclosed herein includes more than one R group, for example, each of the R groups is independently selected as are each R', R", R''', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —$CO_2$R', —CONR'R", —OC (O)NR'R", —NR"C(O)R', —NR'—C(O)NR"R''', —NR"C(O)$_2$R', —NR—C(NR'R"R''')=NR"", —NR—C(NR'R")=NR''', —S(O)R', —S(O)$_2$R', —S(O)$_2$NR'R", —NRSO$_2$R', —NR'NR"R''', —ONR'R", NR'C=(O)NR"NR'''R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R''', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound disclosed herein includes more than one R group, for example, each of the R groups is independently selected as are each R', R", R''', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)— OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth herein.

The term "pharmaceutically acceptable salts" is meant to include salts of the active compounds that are prepared with relatively nontoxic acids or bases, depending on the particular substituents found on the compounds described herein. When compounds disclosed herein contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds disclosed herein contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds disclosed herein contain both basic and acidic functionalities that allow the compounds to be converted into either base or acid addition salts. Other pharmaceutically acceptable carriers known to those of skill in the art are suitable for the compositions disclosed herein. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds disclosed herein may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, therapeutic agents) to a biological system (e.g. in a subject).

Certain compounds disclosed herein can exist in unsolvated forms as well as solvated forms, including hydrated forms. In general, the solvated forms are equivalent to unsolvated forms and are encompassed within the scope of the present disclosure. Certain compounds disclosed herein may exist in multiple crystalline or amorphous forms. In general, all physical forms are equivalent for the uses contemplated by the present disclosure and are intended to be within the scope of the compositions disclosed herein.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds disclosed herein possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds disclosed herein do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds disclosed herein may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds disclosed herein may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present disclosure, whether radioactive or not, are encompassed within the scope of the present disclosure.

The symbol " $\sim\!\!\sim$ " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds disclosed herein are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a symptom associated with a disease (e.g. viral infection) means that the symptom of the disease is caused by (in whole or in part) the disease.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein or enzyme.

"Patient" or "subject in need thereof" or "subject" refer to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds disclosed herein. One of skill in the art will recognize that other pharmaceutical excipients are useful in the compositions disclosed herein.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g. antiviral agent). The compound disclosed herein can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions disclosed herein may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of disclosed herein can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions disclosed herein can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions disclosed herein can also be delivered as nanoparticles.

Pharmaceutical compositions provided herein include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of viral infection). Determination of a therapeutically effective amount of a compound disclosed herein is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of viral infection), kind of concurrent treatment, complications from the disease being treated or other health-related problems. Other therapeutic regimens or agents can be used in conjunction with the methods and compounds disclosed herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating viral infection, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In embodiments, the compounds described herein may be combined with other anti-viral agents.

The term "about" in the context of a numerical value means the nominal numerical value±10% thereof, unless expressly indicated otherwise.

Pharmaceutical Compositions

In a first aspect, there is provided a pharmaceutical composition including a pharmaceutical acceptable carrier, an N-acetylcysteine or derivative thereof and antioxidant compound.

In embodiments, the antioxidant compound is present in an amount sufficient (or effective) to reduce oxidation of the N-acetylcysteine or derivative thereof relative to the absence of the antioxidant. In embodiments, the pH of the composition (also referred to herein as a formulation and vice versa) adjusted to reduce oxidation of the N-acetylcysteine or derivative thereof. In embodiments, the formulations provided herein includes a free radical scavenging compound or a free radical inhibiting compound, such as but not limited to mannitol, BHT, BHA, TBHQ, hydroquinone, urea, tocopherol, $Fe^{3+}$-EDTA. In embodiments, the amount of free radical scavenging compound or a free radical inhibiting compound is provided in an amount to reduce oxidation of the N-acetylcysteine or derivative thereof relative to the absence of the free radical scavenging compound or a free radical inhibiting compound. In embodiments, the formulations are stabilized for a sufficient amount of time to allow treatment within the methods described herein. For example, in embodiments the N-acetylcysteine or derivative thereof is not significantly degraded for at least 1 to 180 or more days when stored at approximately room temperature. The term "not significantly degraded" as used herein means that at least 75% of the N-acetylcysteine or derivative thereof remains in the formulations described herein over the specified period of time. In embodiments, at least 80%, 85%, 90%, 95%, 96%, 97%, 98%, 99% or 100% of the N-acetylcysteine or derivative thereof remains in the formulations described herein over the specified period of time. In embodiments, at least 90% of the N-acetylcysteine or derivative thereof remains in the formulations described herein over the specified period of time. In embodiments, at least 95% of the N-acetylcysteine or derivative thereof remains in the formulations described herein over the specified period of time. In embodiments, at least 99% of the N-acetylcysteine or derivative thereof remains in the formulations described herein over the specified period of time. In embodiments, 100% of the N-acetylcysteine or derivative thereof remains in the formulations described herein over the specified period of time. In embodiments of the formulations described in this paragraph, the specified period of time is at least 1 to 90 days, 1 to 45 days, 1 to 30 days, 1 to 15 days, or 1 to 10 days. In embodiments of the formulations described in this paragraph, the specified period of time is about 1 to 180 days, 1 to 90 days, 1 to 45 days, 1 to 30 days, 1 to 15 days, 1 to 10 days. In embodiments of the formulations described in this paragraph, the specified period of time is about 5 to 180 days, 5 to 90 days, 5 to 45 days, 5 to 30 days, 5 to 15 days, 5 to 10 days. In embodiments of the formulations described in this paragraph, the specified period of time is about 10 to 180 days, 10 to 90 days, 10 to 45 days, 10 to 30 days, or 10 to 15 days. In embodiments of the formulations described in this paragraph, the specified period of time is at least 5 days, at least 10 days, at least, 15 days, at least 30 days, at least 45 days, at least 90 days, at least 120 days, at least 150 days, at least 180 days or at least 360 days. In embodiments of the formulations described in this paragraph, the specified period of time is at least 5 days. In embodiments of the formulations described in this paragraph, the specified period of time is at 10 days. In embodiments of the formulations described in this paragraph, the specified period of time is at 15 days. In embodiments of the formulations described in this paragraph, the specified period of time is at 30 days. In embodiments of the formulations described in this paragraph, the specified period of time is at 45 days. In embodiments of the formulations described in this paragraph, the specified period of time is at 90 days. In embodiments of the formulations described in this paragraph, the specified period of time is at 120 days. In embodiments of the formulations described in this paragraph, the specified period of time is at 150 days. In embodiments of the formulations described in this paragraph, the specified period of time is at 180 days. In embodiments of the formulations described in this paragraph, the specified period of time is at 360 days.

In embodiments, the pharmaceutical composition is non-aqueous. In embodiments, the pharmaceutical composition is aqueous. The term "aqueous" in this context refers, in the usual and customary sense, to the inclusion of water. The term "non-aqueous" in this context refers, in the usual and customary sense, to a composition which does not include water during manufacture or formulation (e.g., substantially less than 1% w/w, e.g., trace amounts). In embodiments, the pharmaceutical composition is an aqueous composition comprising less than about 10% w/w of water. In embodiments, the pharmaceutical composition is an aqueous composition comprising less than about 9% w/w of water. In embodiments, the pharmaceutical composition is an aqueous composition comprising less than about 8% w/w of water. In embodiments, the pharmaceutical composition is an aqueous composition comprising less than about 7% w/w of water. In embodiments, the pharmaceutical composition is an aqueous composition comprising less than about 6% w/w of water. In embodiments, the pharmaceutical composition is an aqueous composition comprising less than about 5% w/w of water. In embodiments, the pharmaceutical composition is an aqueous composition comprising less than about 4% w/w of water. In embodiments, the pharmaceutical composition is an aqueous composition comprising less than about 3% w/w of water. In embodiments, the pharmaceutical composition is an aqueous composition comprising less than about 2% w/w of water. In embodiments, the pharmaceutical composition is an aqueous composition comprising less than about 1% w/w of water. In embodiments, the pharmaceutical composition is an aqueous composition comprising less than about 0.5% w/w of water. In embodiments, the pharmaceutical composition is an aqueous composition comprising less than about 0.1% w/w of water.

In embodiments, the pharmaceutical composition is a liquid or semi-solid composition. In embodiments, the liquid or semi-solid composition is a lotion, gel, cream or ointment.

Further to any embodiment disclosed herein, in embodiments the pharmaceutical acceptable carrier is arachidyl glycol, butoxypropanol, butylene glycol, butyloctanol, calcium gluconate, caprylyl glycol, diglycerin (oxybispropanediol), ethoxydiglycol, glycerol, glycereth-7, glycereth-12, glycereth-20, glycereth-26, glycereth-31, hexacosyl glycol, 1, 2, 6-hexanetriol, hydroxyethyl sorbitol, sorbitol, mannitol, methoxy PEG-10, methoxy PEG-16, methoxy PEG-40, methoxy PEG-100, monoglycride citrate, erythritol, triglycerol, trehalose, xylitol, glyceryl triacetate, propylene glycol, propylene carbonate, a polyethylene glycol, a polymeric polyol, polyglycerol sorbitol, GLUCAM™ P20 (PPG-20 Methyl Glucose Ether), GLUCAM™ E20 (methyl gluceth-20), phytantriol, maltitol, isopentyldiol (aka, 1,1-dimethyl-1,3-propane diol), 1,3-propanediol, or a plant extract. In embodiments, the pharmaceutical composition includes a plurality of carriers as set forth herein. In embodiments, the pharmaceutical composition includes 2, 3, 4, 5 or more carriers as set forth herein. In embodiments, the pharmaceutical composition includes two to three to four carriers as set forth herein. In embodiments, the pharmaceutical acceptable carrier is glycerol (e.g. anhydrous glycerol/glycerin).

Further to any embodiments disclosed herein, in embodiments, the antioxidant is acetyl cysteine, acetyl trihexylcitrate, arbutin, ascorbic acid, ascorbic acid polypeptide, ascorbyl dipalmitate, ascorbyl methylsilanol pectinate, ascorbyl palmitate, ascorbyl stearate, betalains (betanin), betaxanthine (e.g., indicaxanthine) BHA, BHT, t-butyl hydroquinone, calcium ascorbate, chitosan salicylate, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate other monovalent or divalent salts of ascorbyl phosphate, methylsilanol ascorbate, natural botanical anti-oxidants such as green tea or grape seed extracts, nordihydroguaiaretic acid, octyl gallate, phenylthioglycolic acid, potassium ascorbate, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiomorpholinone, thiosalicylic acid, thiotaurine, thioxanthine, tocophereth-5, tocophereth-10, tocophereth-12, tocophereth-18, tocophereth-50, tocopherol, tocophersolan, tocopheryl acetate, tocopheryl linoleate, tocopheryl nicotinate, tocoquinone, tocopheryl succinate, triethyl citrate, tris (nonylphenyl)phosphite, ubiquinone, zinc dibutyldithiocarbamate, ascorbyl-2-phosphate and ascorbyl polyphosphate and the respective salts thereof, allantoin ascorbate, ascorbyl tocopheryl maleate, potassium ascorbyl tocopheryl phosphate, tetrahexyldecyl ascorbate, tetra hydrodiferuloylmethane, caffeic acid, caffeoylquinic acid (from *Scheffera Heptphylla*) (L.) *Frodin*) in particular 3-O-caffeoyl quinic acid, melatonin, thiotaurine, ortho tolyl biguanidine, telmesteine, aconitic acid, cat's claw chaste tree, trolox, pyruvic acid, glycolic acid, lactic acid, polylactic acid, beta-hydroxy acids e.g, beta-hydroxybutyric acid, anoxomer, ferrous sulfate, lipoic acid, carnosic acid, chlorogenic acid, carnosine, lysine, histidine HCl, phytosteryl linoleate, phytosteryl linoleate/linolenate, formaldehyde sulfoxylate, alcloxa, iron, zinc, aluminum, rutin, quercetin, thiodipropionic acid, TENOX™ (mixtures of BHT and/or BHA and/or TBHQ (tert-butyl-hydroquinone) and/or citric acid), narigenin, succinic acid, maleic acid, dehydroacetic acid. In embodiments, the pharmaceutical composition includes one antioxidant as set forth herein. In embodiments, the pharmaceutical composition includes a plurality of antioxidants as set forth herein. In embodiments, the pharmaceutical composition includes 2, 3, 4, 5, or more antioxidants as set forth herein. In embodiments, the pharmaceutical composition includes two antioxidants as set forth herein.

In embodiments, the antioxidant is ascorbic acid. In embodiments, the molar ratio of N-acetylcysteine to ascorbic acid is in the range from 2200:1 to 2:1. In embodiments, the molar ratio of N-acetylcysteine to ascorbic acid is in the range 1000:1 to 2:1, 900:1 to 2:1, 800:1 to 2:1, 700:1 to 2:1, 600:1 to 2:1, 500:1 to 2:1, 400:1 to 2:1, 300:1 to 2:1, 200:1 to 2:1, 100:1 to 2:1, 90:1 to 2:1, 80:1 to 2:1, 70:1 to 2:1, 60:1 to 2:1, 50:1 to 2:1, 40:1 to 2:1, 30:1 to 2:1, 20:1 to 2:1, or 10:1 to 2:1. In embodiments, the molar ratio of N-acetylcysteine to ascorbic acid is in the range of 540:1 to 2:1. In embodiments, the ascorbic acid is in the range of about 0.01 to 5.0 (w/w %), 0.1 to 4.0 (w/w %), 0.1 to 3.0 (w/w %), 0.1 to 2.0 (w/w %), or 0.1 to 1.0 (w/w %). In embodiments, the ascorbic acid is in the range of about 0.2 to 5.0 (w/w %), 0.2 to 4.0 (w/w %), 0.2 to 3.0 (w/w %), 0.2 to 2.0 (w/w %), or 0.2 to 1.0 (w/w %). In embodiments, the ascorbic acid is in the range of about 0.3 to 5.0 (w/w %), 0.3 to 4.0 (w/w %), 0.3 to 3.0 (w/w %), 0.3 to 2.0 (w/w %), or 0.3 to 1.0 (w/w %). In embodiments, the ascorbic acid is in the range of about 0.4 to 5.0 (w/w %), 0.4 to 4.0 (w/w %), 0.4 to 3.0 (w/w %), 0.4 to 2.0 (w/w %), or 0.4 to 1.0 (w/w %). In embodiments, the ascorbic acid is in the range of about 0.5 to 5.0

(w/w %), 0.5 to 4.0 (w/w %), 0.5 to 3.0 (w/w %), 0.5 to 2.0 (w/w %), or 0.5 to 1.0 (w/w %). In embodiments, the ascorbic acid is about 0.1, 0.2, 0.3, 0.4, 0.5, 0.6, 0.7, 0.8, 0.9 or 1.0 (w/w %). In embodiments, the ascorbic acid is about 0.5 (w/w %).

In embodiments, the antioxidant is caffeic acid. In embodiments, the antioxidant is glutamic acid. In embodiments, the antioxidant is succinic acid. In embodiments, the antioxidant is maleic acid. In embodiments, the antioxidant is lactic acid. In embodiments, these acids may additionally or alternatively function as pH adjusters. The term "pH adjuster" and the like refer, in the usual and customary sense, to a composition useful to change or adjust the pH of another composition to a desired pH. The pH adjuster may be in any form (e.g., liquid, solid, dispersion, and the like) useful for admixture with the other composition. The pH adjuster may be dissolved or dispersed in an aqueous solvent. The pH adjuster may be dissolved or dispersed in an organic solvent. The pH adjuster may be dissolved or dispersed in an anhydrous organic solvent. Further to any aspect or embodiment thereof disclosed herein, in embodiments, the antioxidant is in the range of about 0.01 to 5.0 (w/w %), 0.1 to 4.0 (w/w %), 0.1 to 3.0 (w/w %), 0.1 to 2.0 (w/w %), or 0.1 to 1.0 (w/w %). In embodiments, the antioxidant is in the range of about 0.2 to 5.0 (w/w %), 0.2 to 4.0 (w/w %), 0.2 to 3.0 (w/w %), 0.2 to 2.0 (w/w %), or 0.2 to 1.0 (w/w %). In embodiments, the antioxidant is in the range of about 0.3 to 5.0 (w/w %), 0.3 to 4.0 (w/w %), 0.3 to 3.0 (w/w %), 0.3 to 2.0 (w/w %), or 0.3 to 1.0 (w/w %). In embodiments, the antioxidant is in the range of about 0.4 to 5.0 (w/w %), 0.4 to 4.0 (w/w %), 0.4 to 3.0 (w/w %), 0.4 to 2.0 (w/w %), or 0.4 to 1.0 (w/w %). In embodiments, the antioxidant is in the range of about 0.5 to 5.0 (w/w %), 0.5 to 4.0 (w/w %), 0.5 to 3.0 (w/w %), 0.5 to 2.0 (w/w %), or 0.5 to 1.0 (w/w %). In embodiments, the antioxidant is about 0.1, 0.2, 0.3, 0.4, 0.5, 0.6, 0.7, 0.8, 0.9 or 1.0 (w/w %). In embodiments, the antioxidant is about 0.5 (w/w %).

In embodiments, the formulation includes a preservative. In embodiments, the preservative is benzalkonium chloride. In embodiments, benzalkonium chloride is present in the range of about 0.01 to 1.0 (w/w %), 0.01 to 0.9 (w/w %), 0.01 to 0.8 (w/w %), 0.01 to 0.7 (w/w %), 0.01 to 0.6 (w/w %), 0.01 to 0.5 (w/w %), 0.01 to 0.4 (w/w %), 0.01 to 0.3 (w/w %), 0.01 to 0.2 (w/w %), or 0.01 to 0.1 (w/w %), In embodiments, benzalkonium chloride is present in the range of 0.1 to 1.0 (w/w %), 0.1 to 0.9 (w/w %), 0.1 to 0.8 (w/w %), 0.1 to 0.7 (w/w %), 0.1 to 0.6 (w/w %), 0.1 to 0.5 (w/w %), 0.1 to 0.4 (w/w %), 0.1 to 0.3 (w/w %), or 0.1 to 0.2 (w/w %). In embodiments, benzalkonium chloride is present at about 0.10, 0.11, 0.12, 0.13, 0.14 or 0.15 (w/w %). In embodiments, benzalkonium chloride is present at about 0.120, 0.122, 0.124, 0.126, 0.128, 0.130, 0.132, 0.134, 0.136, 0.138 or 0.140 (w/w %). In embodiments, benzalkonium chloride is present at about 0.136 (w/w %).

In embodiments, the amount of the antioxidant is sufficient to reduce oxidation of the N-acetylcysteine or derivative thereof by at least 10%, 20%, 30%, 40% 50%, 60%, 70%, 80%, 90% or 99% relative to the absence of the antioxidant over a period of at least 1, 7, 14, 30, 60, 90, 120, 365 or 730 days at a storage temperature of about 20° C. to 30° C. In embodiments, the amount of the antioxidant is sufficient to reduce oxidation of the N-acetylcysteine or derivative thereof by at least 50%, 60%, 70%, 80%, 90% or 99% relative to the absence of the antioxidant over a period of at least 1, 7, 14, 30, 60, 90, 120, 365 or 730 days at a storage temperature of about 20° C. to 30° C. In embodiments, the storage temperature is about 20° C., 21° C., 22° C., 23° C., 24° C., 25° C., 26° C., 27° C., 28° C., 29° C. or 30° C. In embodiments, the storage temperature is about 25° C.

In embodiments, the pharmaceutical composition is within a container that is substantially free of oxygen gas. In embodiments, the container includes an inert gas. In embodiments, the inert gas is nitrogen or argon.

In embodiments, the pharmaceutical composition further includes a pH adjuster. In embodiments, the pH adjuster is an inorganic acid, e.g., HCL, or an inorganic base, e.g., NaOH or KOH. In embodiments, the pH adjuster is prepared in anhydrous organic solvent.

In embodiments, the pharmaceutical composition is a topical pharmaceutical composition.

In embodiments, the N-acetylcysteine or derivative thereof is present at a concentration of about 0.1% w/w to about 20% w/w. In embodiments, the concentration of N-acetylcysteine or derivative thereof is about 0.1%, 0.2%, 0.3%, 0.4%, 0.5%, 0.6%, 0.7%, 0.8%, 0.9%, 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, or 20.0%.

In embodiments, the N-acetylcysteine or derivative thereof is an N-acetylcysteine salt, N-acetylcysteine ester, N-acetylcysteine amide or N-acetylcysteine metal thiol chelate. In embodiments, the chelate may be $ZnCl_2$, $ZnO$, $Zn(acetate)_2$ and the like, as known in the art.

In embodiments, the pharmaceutical composition further includes a silica, silicate, silicic acid, silatrane glycol, metal silicate, alumina or aluminate. In embodiments, the silica, silicate, silicic acid, silatrane glycol, metal silicate, alumina or aluminate is present at about 0.01 to 50.00 (w/w %), 0.01 to 40.00 (w/w %), 0.01 to 30.00 (w/w %), 0.01 to 20.00 (w/w %), 0.01 to 10.00 (w/w %), 0.01 to 5.00 (w/w %), 0.01 to 4.00 (w/w %), 0.01 to 3.00 (w/w %), 0.01 to 2.00 (w/w %), 0.01 to 1.00 (w/w %), 0.10 to 5.00 (w/w %), 0.10 to 4.00 (w/w %), 0.10 to 3.00 (w/w %), 0.10 to 2.00 (w/w %), 0.10 to 1.00 (w/w %), 1.00 to 5.00 (w/w %), 1.00 to 4.00 (w/w %), 1.00 to 3.00 (w/w %), or 2.00 to 3.00 (w/w %). In embodiments, the silica, silicate, silicic acid, silatrane glycol, metal silicate, alumina or aluminate is present at about 2.50, 2.60, 2.70, 2.80 2.90 or 3.00 (w/w %). In embodiments, the silica, silicate, silicic acid, silatrane glycol, metal silicate, alumina or aluminate is present at about 2.83 (w/w %).

In embodiments, the pharmaceutical composition further includes a gelling agent, as known in the art. In embodiments, the gelling agent is CARBOPOL® Ultrez 30 (i.e., INCI designation carbomer, cross-linked homopolymer of acrylic acid), CARBOPOL® Ultrez 10 (INCI designation carbomer, cross-linked homopolymer of acrylic acid), CARBOPOL® Ultrez 21 (INCI designation acrylates/C10-30 alkyl acrylate crosspolymer, with hydrophobically modified crosslinked polyacrylate polymer) or mixtures thereof. In embodiments, the gelling agent is present in the range of about 0.01 to 2.000 (w/w %), 0.01 to 1.500 (w/w %), 0.01 to 1.000 (w/w %), 0.01 to 0.900 (w/w %), 0.01 to 0.800 (w/w %), 0.01 to 0.700 (w/w %), 0.01 to 0.600 (w/w %), 0.01 to 0.500 (w/w %), 0.01 to 0.400 (w/w %), 0.01 to 0.300 (w/w %), 0.01 to 0.200 (w/w %), or 0.01 to 0.100 (w/w %). In embodiments, the gelling agent is present at about 0.10 to 0.500 (w/w %), 0.10 to 0.400 (w/w %), 0.10 to 0.300 (w/w %), or 0.10 to 0.200 (w/w %). In embodiments, the gelling agent is present at about 0.150, 0.160, 0.170, 0.180 0.190 or 0.200 (w/w %). In embodiments, the gelling is agent is present at about 0.189 (w/w %).

In embodiments, the pharmaceutical composition further includes a dental paste.

In embodiments, the pharmaceutical composition is a non-aqueous pharmaceutical composition.

In another aspect, there is provided a pharmaceutical formulation including an N-acetylcysteine or derivative thereof.

In embodiments, the pharmaceutical formulation further includes a non-aqueous liquid carrier. In embodiments, the non-aqueous liquid carrier is glycerol, sorbitol, mannitol, erythritol, xylitol, glyceryl triacetate, propylene glycol, a polyethylene glycol, a polymeric polyol or a plant extract. In embodiments, the non-aqueous liquid carrier is glycerol. Further to any embodiment disclosed herein, in embodiments the pharmaceutical acceptable carrier is arachidyl glycol, butoxypropanol, butylene glycol, butyloctanol, calcium gluconate, caprylyl glycol, diglycerin (Oxybispropanediol), ethoxydiglycol, glycerol, glycereth-7, glycereth-12, glycereth-20, glycereth-26, glycereth-31, hexacosyl glycol, 1, 2, 6-hexanetriol, hydroxyethyl sorbitol, sorbitol, mannitol, methoxy PEG-10, methoxy PEG-16, methoxy PEG-40, methoxy PEG-100, monoglycride citrate, erythritol, triglycerol, trehalose, xylitol, glyceryl triacetate, propylene glycol, propylene carbonate, a polyethylene glycol, a polymeric polyol, polyglycerol sorbitol, GLUCAM™ P20, GLUCAM™ E20, phytantriol, maltitol, isopentyldiol (aka, 1,1-dimethyl-1,3-propane diol), 1,3-propanediol, or a plant extract. In embodiments, the pharmaceutical composition includes a plurality of carriers as set forth herein. In embodiments, the pharmaceutical composition includes 2, 3, 4, 5, or more carriers as set forth herein. In embodiments, the pharmaceutical composition includes two to three to four carriers as set forth herein.

In embodiments, the non-aqueous or aqueous pharmaceutical formulation is within a container that is substantially free of oxygen gas. In embodiments, the non-aqueous pharmaceutical formulation is within a container that is substantially free of oxygen gas. In embodiments, the container includes an inert gas. In embodiments, the container includes nitrogen gas or argon gas. In embodiments, the pharmaceutical formulation does not include an antioxidant. In embodiments, the pharmaceutical formulation does not include ascorbic acid or derivative thereof. In embodiments, the pharmaceutical composition is an anhydrous pharmaceutical composition.

In embodiments, the pharmaceutical composition includes anhydrous degassed glycerin, ascorbic acid, and NAC. In embodiments, pharmaceutical composition includes anhydrous degassed glycerin, ascorbic acid, fused silica, and NAC. In embodiments, the pharmaceutical composition includes anhydrous degassed glycerin, ascorbic acid, NAC, and aqueous NaOH or HCl to adjust pH. In embodiments, the pharmaceutical composition includes anhydrous degassed glycerin, ascorbic acid, NAC, and aqueous NaOH, HCl and/or phosphate-citrate and/or acetate buffer to adjust pH. In embodiments, the pharmaceutical composition includes anhydrous degassed glycerin, ascorbic acid, NAC, aqueous NaOH, HCl and/or phosphate citrate buffer to adjust pH, and optionally benzalkonium chloride. In embodiments, the pharmaceutical composition includes anhydrous degassed glycerin, ascorbic acid, NAC, aqueous NaOH, HCl or sodium acetate to adjust pH, and optionally benzalkonium chloride. In embodiments, the pharmaceutical composition includes anhydrous degassed glycerin, ascorbic acid, NAC, aqueous NaOH, HCl to adjust pH, and optionally benzalkonium chloride. In embodiments, the pharmaceutical composition includes anhydrous degassed glycerin, ascorbic acid, NAC, aqueous NaOH, HCl or phosphate citric acid to adjust pH, and optionally benzalkonium chloride. In embodiments, the pharmaceutical composition includes anhydrous degassed glycerin, ascorbic acid, NAC, aqueous NaOH or HCl to adjust pH, and optionally benzalkonium chloride. In embodiments, the pharmaceutical composition includes anhydrous degassed glycerin, ascorbic acid, NAC, aqueous NaOH or HCl to adjust pH, optionally benzalkonium chloride, and a gelling agent. In embodiments, the pharmaceutical composition includes anhydrous degassed glycerin, ascorbic acid, NAC, aqueous NaOH, HCl and/or phosphate citrate to adjust pH, optionally benzalkonium chloride, and a further excipient selected from one or more of ascorbyl palmitate, lactic acid, glutamic acid, lipoic acid, and mannitol. In embodiments, the pharmaceutical composition includes anhydrous degassed glycerin, ascorbic acid, NAC, benzalkonium chloride, and one or more further excipient selected from sorbitan sesquioleate, lipoic acid, ascorbyl palitate, mannitol, optionally including NaOH in anhydrous glycerin. In embodiments, the pharmaceutical composition includes anhydrous degassed glycerin, ascorbic acid, NAC, optionally benzalkonium chloride, and one or more further excipient selected from sorbitan monooleate, sorbitan sesquioleate, lipoic acid, ascorbyl palitate, mannitol, optionally including NaOH in anhydrous glycerin or phosphate citrate buffer. In embodiments, the pharmaceutical composition includes anhydrous degassed glycerin PEG300, PEG400 or PEG600, ascorbic acid, NAC, and aqueous NaOH, HCl and/or phosphate citrate buffer. In embodiments, the pharmaceutical composition includes anhydrous degassed glycerin, PEG300, PEG400 or PEG600, ascorbic acid, NAC, and aqueous NaOH, HCl and/or phosphate citrate buffer. In embodiments, the pharmaceutical composition includes anhydrous degassed glycerin, a gelling agent (e.g., GLUCAM™ P20, ascorbic acid, NAC, and aqueous NaOH or HCl. In embodiments, the pharmaceutical composition includes anhydrous degassed glycerin, ascorbic acid, NAC, CARBOPOL® Ultrez 30, and aqueous NaOH or HCl. In embodiments, the pharmaceutical composition includes anhydrous degassed glycerin, ascorbic acid, NAC, CARBOPOL® Ultrez 30, and aqueous NaOH, HCl and/or phosphate citrate buffer.

In another aspect, there is provided a dermal patch including an N-acetylcysteine or derivative thereof and an amount of an antioxidant compound sufficient to reduce oxidation of the N-acetylcysteine or derivative thereof relative to the absence of the antioxidant.

In another aspect, there is provided a method of treating a herpesvirus infection in a subject. The method includes administering an effective amount of a pharmaceutical composition or a dermal patch as disclosed herein to a subject in need thereof. In embodiments, the herpesvirus is herpes zoster.

In embodiments, the administering is topically administering.

In embodiments, the herpesvirus infection in the subject presents as a cold sore, genital herpes, or shingles.

In embodiments, the subject presents no symptoms of the herpesvirus infection within 2 to 10 days of the administration.

In another aspect, there is provided a method of treating a canker sore in a subject. The method includes administering an effective amount of a pharmaceutical composition or a dermal patch as disclosed herein to a subject in need thereof.

In another aspect, there is provided a method for preparing a pharmaceutical composition. The method includes mixing an N-acetylcysteine or derivative thereof with a liquid pharmaceutical carrier within a container, wherein the liquid pharmaceutical carrier is anhydrous (e.g. pre-dominantly anhydrous) and substantially free of oxygen gas.

In embodiments, the container contains an inert gas and is sealed from ambient air. In embodiments, the inert gas is argon or nitrogen.

The mechanisms described herein are provided to further elucidate embodiments of the compositions provided here and are not intended to limit any aspect thereof. In embodiments, the active ingredient and formulation stability enhancing agents can be used to improve the shelf life of the desired and described topical formulations within the scope of this disclosure. Of particular interest is stability enhancing agents that are antioxidants. Since thiols in general are prone to oxidation, the use of sacrificial antioxidants can play an important role in improving the stability of an active 'thiol' feature. In embodiments, the sacrificial antioxidant is does not cross react with the active or inactive agents present in the final formulation. Furthermore, in embodiments, the reduced product(s) that is generated from an antioxidant agent that is selected as a sacrificial antioxidant does not cross react with active or inactive agents present in the final formulation. The selected sacrificial antioxidant may also be chosen such that its reduced product is not detrimental to the overall effectiveness of the active ingredient or the final formulation itself.

For example, when choosing a sacrificial antioxidant to prevent the oxidation of N-acetylcysteine or cysteine, the experimentally determined oxidation-reduction potentials of N-acetylcysteine or cysteine may be used to choose the appropriate antioxidant(s) that would be preferentially oxidized over N-acetylcysteine or cysteine or the pertinent thiol. In embodiments, the antioxidant is ascorbic acid or derivative thereof, such as ascorbyl-2-glucoside (ASC-G), ascorbic acid 2-phosphate, ascorbic acid 2-sulfate, ascorbyl-6-octanoate (ASC-8), ascorbyl laurate, ascorbyl myristate, ascorbyl-6-palmitate (ASC-P), ascorbyl-6-stearate (ASC-S), (ascorbic acid/kojic acid, ascorbic acid/ferulic acid and ascorbic acid/alpha-tocopherol) hybrids or ascorbyl-2,6-dipalmitate (ASC-DP). In embodiments, the antioxidant is ascorbic acid or derivative thereof, such as ascorbyl-2-glucoside (ASC-G), ascorbic acid 2-sulfate, ascorbyl-6-octanoate (ASC-8), ascorbyl laurate, ascorbyl myristate, ascorbyl-6-palmitate (ASC-P), ascorbyl-6-stearate (ASC-S), (ascorbic acid/kojic acid, ascorbic acid/ferulic acid and ascorbic acid/alpha-tocopherol) hybrids or ascorbyl-2,6-dipalmitate (ASC-DP). In embodiments, the antioxidant is ascorbic acid or derivative thereof, such as ascorbyl-2-glucoside (ASC-G), ascorbic acid 2 phosphate, ascorbic acid 2-sulfate, ascorbyl-6-octanoate (ASC-8), ascorbyl laurate, ascorbyl myristate, ascorbyl-6-palmitate (ASC-P), ascorbyl-6-stearate (ASC-S), (ascorbic acid/kojic acid, ascorbic acid/ferulic acid and ascorbic acid/alpha-tocopherol) hybrids or ascorbyl-2,6-dipalmitate (ASC-DP). In embodiments, the antioxidant is ascorbic acid or derivative thereof not disclosed in U.S. Published Appl. US 2012/0135062.

In embodiments, the effectiveness of ascorbic acid and the aforementioned derivatives are synergistic (i.e., antioxidant activity is enhanced) when combined with other antioxidants. In embodiments, the effectiveness of ascorbic acid and the aforementioned derivatives are synergistic in stabilizing NAC when combined with other antioxidants. The hydrophilic ascorbic acid derivatives may be suitable for nano-emulsions, heterogeneous solutions including aggregated systems (micelles, liposomes, and microemulsions). Furthermore it is noteworthy to mention that certain ascorbic acid derivatives with a fatty acid side chain could enhance dermal skin permeability. A typical formulation could contain about 0.01% to 2% of the sacrificial antioxidant based on w/w of the final formulation.

In embodiments, the formulations provided here comprises a metal. Metals may be present in formulations as a cationic species such as $Ca^+$ (e.g. as $CaCl_2$) or $Zn^{2+}$ (e.g. as ZnO or $ZnSO_4$). In embodiments, when ascorbic acid is included in combination with a cationic metal species such as those containing Cu and Fe, a metal cationic species complexing agent is provided such as EDTA or citric acid.

In embodiments, the formulations provided herein include a reducing metals. Reducing metals may be present in their elemental form such as Fe, Zn, Al. Such metals may be included in various formulations such as a strip, powder (nano or micronized or large, medium or fine mesh size) or in a suitable solid form such as spheres or beads or polymeric beads coated with metal.

In embodiments, the formulations provided herein include a reducing agent such as aminoethanesulfinic acid, ammonium sulfate, ammonium thiolactate, ammonium thioglycolate, calcium thioglycolate, cysteine or cysteine salts, dithioglycolate, magnesium thioglycolate, potassium thioglycolate, sodium thioglycolate, strontium thioglycolate, ethanolamine dithioglycolate, ethanolamine thioglycolate, glyceryl thiopropionate, hydroquinone, lysine HCl, mercaptopropionic acid, thioglycerin, thioglycolic acid, histidine HCl, cysteamine, dihydroxy acetone, stannous chloride or thiomorpholinone. In embodiments, the formulation includes one reducing agent as set forth herein. In embodiments, the formulation includes a plurality of reducing agents as set forth herein. In embodiments, the formulation includes 2, 3, 4, 5, or more reducing agents as set forth herein. In embodiments, the formulation includes two reducing agents as set forth herein.

In general the pH of final formulations could be adjusted if needed by using appropriate/acceptable acid or base, such as inorganic bases prepared in a non-aqueous media and/or organic bases soluble in non-aqueous medium. In embodiments, the pH is from about 3.0 to about 8.0 (e.g. in glycerin). In embodiments, the pH is from about 3.0 to about 8.0 (e.g. in glycerin). In embodiments, the pH is from about 4.5 to about 5.0 (e.g. in glycerin). In embodiments, the pH is from about 5.0 to about 5.5 (e.g. in glycerin). In embodiments, the pH is from about 5.5 to about 6.0 (e.g. in glycerin). In embodiments, the pH is from about 6.0 to about 6.5 (e.g. in glycerin). In embodiments, the pH is from about 6.5 to about 7.0 (e.g. in glycerin). In embodiments, the pH is from about 7.0 to about 7.5 (e.g. in glycerin). In embodiments, the pH is from about 4.0 to about 6.5 (e.g. in glycerin). In embodiments, the pH is from about 4.0 to about 6.0 (e.g. in glycerin). In embodiments, the pH is from about 4.0 to about 6.0 (e.g. in glycerin). In embodiments, the pH is from about 4.0 to about 5.5 (e.g. in glycerin). In embodiments, the pH is from about 4.0 to about 4.5 (e.g. in glycerin). In embodiments, the pH is from about 4.1 to about 4.5 (e.g. in glycerin).

Some of the formulations disclosed herein provide exact quantities used as well as possible ranges to enable one trained in the art to derive effective formulations. Ranges when provided are not meant to be restrictive in any manner and one trained in the art could adjust the quantities of each ingredient to enable better characteristics and desired outcomes of the formulation.

Discussion

A therapeutically acceptable concentration of the compounds disclosed herein in the formulations disclosed herein is a basic theme of the embodiments. Such concentration inter alia is theorized to destroy the capsid structure of a virus.

While not being bound to any theory, it is proposed that NAC and derivatives thereof when applied topically to HSV-1, HSV-2 and shingles act upon both types of virus life cycle capsids, the immature (DNA containing) and the mature (RNA containing) capsids. Lysing of the virus capsid releases the packaged material which is subsequently susceptible to the host immune system. A formulation that enhances this skin and cell penetration can achieve the lysing more readily.

The envisaged limits concentrations of the active ingredient range from 0.1 to 20%.

The active ingredient of the inventive formulation is selected from the group consisting of N-acetylcysteine (NAC), N-acetyl homocysteine (NAH), N, N'-diacetyl cysteine (DAC), N-acetyl cysteine ethyl ester (NACE) or other derivatives.

In other embodiments, a dermal penetrating enhancer such as DMSO, 2-pyrrolidone, N-methyl pyrolidone and 1,3-dimethyl imidazolindinone, urea, dimethylacetamide, DDAIP (2-Dimethylaminopropionic acid dodecyl ester, DDAIP organic and inorganic salts e.g., HCl salt (CAS #259685-49-9), castor oil, lanolin or the like and their mixtures may be used in the formulation.

In other embodiments, the active ingredient may be micronized to improve mass transfer of the active species cellularly. The active ingredient can also be ground or micronized to a fine size to improve the transfer to the site. When particles are ground finer or micronized, the viscosity of the formulation will increase and may need to be optimized to promote good flux of active ingredient to the infection sites.

In other embodiments, a hydrogen sulfide scavenger, such as a polymer supported transition metal in a chelated or salt form or a polymer supported amine or activated or inactivated carbon in granular or appropriate solid form, can be used in the formulation. Hydrogen sulfide scavengers in these forms offer a distinct advantage in that they are retained within the dispensing container and additionally do not break down or leach the scavenged components.

In other embodiments bulking or formulating agents may be selected from materials (without limitations) such as aloe vera, pectin, cellulose, stearic acid, metal stearates, light mineral oil, maltodextrin, white petroleum, white wax, vitamin D, vitamin A palmitate, emmulgade cm, carbomer, carbopol, medical anti-foam AF emulsion, xanthan gum, sodium carboxymethyl cellulose, gum tragacanth, konjac maanan, guar gum, locust bean gum, tara gum, gum, arabic, karaya gum, gum guaiac, glycerol, glycerol mono and polystearate, other polyols derived from sugar such as sorbitol or xylitol or erythritol or mannitol and ceteareth-15.

In other embodiments the formulation may comprise coloring agents, fragrances, preservatives and other natural or synthetic or semi-synthetic in origin.

In other embodiments all possible permutations and combinations of the above mentioned materials in earlier embodiments may be used to design a formulation.

In other embodiments the active ingredient or formulation can be provided in unit dosage forms for single use or in a form wherein the dose is constituted by breaking or puncturing a barrier between the active ingredient and an acceptable formulation followed by mixing (such as shaking the dispenser) prior to application.

In other embodiments the active ingredient or formulation can be provided in a container system equipped with an airless pump mechanism. Such container systems are commonly referred to as an 'airless tube or pump' which upon activation dispenses the acceptable formulation without allowing the entry of air into the container. Container systems that are significantly air tight and that are designed to reduce or prevent entry of air during or post dispensing of the contained air sensitive formulation are highly suited for commercial use since they can provide or augment the desired product shelf-life.

Further augmentation of shelf-life for the product could be achieved by utilizing appropriate secondary packaging systems such an Aluminum-Mylar pouches with and without an oxygen scavenger packed under an inert gas or vacuum packed and sealed. Optionally the product could be packaged for use in a blow fill seal (BFS) container for single use dispensing or daily use dispensing. If the latter the BFS unit is equipped with as suitable cap for to permit storage during intermittent daily use.

The compositions and methods disclosed herein are applicable to the following diseases or conditions present in mammals. The embodiments described herein could be applied to the infected or targeted area in need of appropriate therapeutic intervention. The dermatological conditions involving skin, mucosal surfaces, ear, nose and eyes are remedied by the application of the disclosed compositions. These conditions include but are not limited to pain, inflammation, adenovirus infections such as viral conjunctivitis (various serotypes) and keratoconjuntivitis, paramyxovirus (RSV), Hendra and Nipha viruses, canine distemper virus, phocine distemper virus, cetacean morbillivirus, rinderpest virus, HSV-1 & 2, shingles, PHN and HPV.

The compositions and methods disclosed herein are applicable to skin conditions such as acne, acne vulgaris, inflammatory acne, non-inflammatory acne, acne fulminans, nodular papulopustular acne, acne conglobate, dermatitis, bacterial skin infections, viral skin infections, parasitic skin infections, skin neoplasia, skin neoplasms, pruritis, cellulitis, acute lymphangitis, lymphadenitis, erysipelas, cutaneous absecces, necrotizing subcutaneous infections, scalded skin syndrome, folliculitis, furuncles, hidradenitis suppurativa, carbuncles, paronychial infections, rashes, ringworm infection, erythrasma, impetigo, erethyma, yeast skin infections, warts, molluscum contagiosum, trauma or injury to the skin, post-operative or post-surgical skin conditions, scabies, pediculosis, creeping eruption, eczemas, psoriasis, pityriasis rosea, lichen planus, pityriasis rubra pilaris, edematous, erythema multiforme, erythema nodosum, granuloma annulare, epidermal necrolysis, sunburn, photosensitivity, pemphigus, bullous pemphigoid, dermatitis herpetiformis, keratosis pilaris, callouses, corns, ichthyosis, skin ulcers, ischemic necrosis, miliaria, hyperhidrosis, moles, Kaposi's sarcoma, melanoma, malignant melanoma, basal cell carcinoma, squamous cell carcinoma, poison ivy, poison oak, contact dermatitis, atopic dermatitis, rosacea, purpura, moniliasis, candidiasis, baldness, alopecia, Behcet's syndrome, cholesteatoma, Dercum disease, ectodermal dysplasia, gustatory sweating, nail patella syndrome, lupus, hives, hair loss, Hailey-Hailey disease, chemical or thermal skin burns, scleroderma, aging skin, wrinkles, sun spots, necrotizing fasciitis, necrotizing myositis, gangrene, scarring, and vitiligo.

In embodiments, the disclosed compositions are suitable for treating a disorder of a localized body surface (e.g., groin), body cavity or mucosal surface, e.g., the mucosa of the nose, mouth, eye, ear, respiratory system, vagina or rectum. Non limiting examples of such conditions include chlamydia infection, gonorrhea infection, hepatitis B, herpes (HSV-1 & 2), shingles, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometriosis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, post-operative ear healing, fecal incontinence, constipation, polyps of the colon and rectum.

In embodiment, the composition is useful for the treatment of an infection. In one or more embodiments, the composition is suitable for the treatment of an infection, selected from the group of a bacterial infection, a fungal infection, a yeast infection, a viral infection and a parasitic infection.

In embodiments, the composition is useful for the treatment of insect bites, poison ivy or oak, wound, ulcer and burn. This use is particularly important since the disclosed composition creates a thin, semi-occlusive layer, which coats the damaged tissue, while allowing exudates to be released from the tissue.

In embodiments, the composition is useful for the treatment and management of pain due to or associated with aforementioned conditions. Additional topical analgesic agents such as allantoin, allyl isothiocyanate, aspirin, aluminum chloride hexahydrate, aspirin, benzethonium chloride, benzocaine, bismuth sodium tartarate, benzyl alcohol, boric acid, bithional, butamben picrate, calamine, camphor, camphorated metacresol, capsaicin, capsicum, capsicum oleoresin, cetalkanium chloride, chloral hydrate, chloralbutanol, chlorpheniramine maleate, creosote, beechwood, cupric sulfate, cyclomethycainesulfate, dexpanthenol, dibucaine beta-HCl, diclofenac, dimethisoquin HCl, diperodon HCl, dyclonine hydrochloride, ephedrine HCl, ergot fluid extract, eucalyptol, eucalyptus oil, eugenol, ferric chloride, glycol salicylate, hectorite, hexylresorcinol, histamine di-HCl, hydrocortisone, hydrocortisone-acetate, impatiens biflora tincture, iron oxide, isopropyl alcohol, juniper tar, lanolin, menthol, merbromin, mercuric chloride, methapyrilene HCl, methylnicotinate, methyl salicylate, panthenol, parethoxycaine HC, pectin, peppermint oil, phenol, phenolate sodium, phenyltoloxamine citrate, povidone-vinylacetate copolymers, pramoxine HCl, pyrilamine maleate, resorcinol, salicylamide, salicylic acid, simethicone, sodium bicarbonate, sodium borate, sulfur, tannic acid, tetracaine, tetracaine HCl, thymol, topical starch, tripelennamine HCl, trolamine, trolamine salicylate, turpentine oil, zinc acetate, zinc oxide, zinc sulfate, zirconium oxide, and the like can be combined and used with the compositions disclosed herein.

In particular the compositions disclosed herein can treat primary or secondary medical conditions more specifically a 'skin condition' arising from or such as acrodermatitis, crodermatitis enteropathica, Atopic dermatitis, Actinomycosis, Aphthous ulcer, Acute necrotizing ulcerative gingivitis, BK-virus nephropathy, Behcet's disease, Castleman's disease (Suspected to be caused by a virus; lymphoproliferative disease), Congenital herpes simplex, Congenital ichthyosis, microcephalus, quadriplegia, Congenital ichtyosiform erythroderma, Congenital mixovirus, Congenital mumps, Congenital porphyria, Congenital varicella syndrome, Cutaneous lupus erythematosus, Cytomegalic inclusion disease, Cytomegalovirus retinitis, Darier disease, Degos disease, Degos 'en cocarde' erythrokeratoderma, dermal eccrine cylindroma, dermatitis herpetiformis familial, dermatocardioskeletal syndrome Boronne type, dermatofibromann dermatofibrosarcoma protuberans, dermatoleukodystrophyn, dermatomyositis, Dermatoosteolysis Kirghizian type, Dermatopathia pigmentosa reticularis Dermochondrocorneal dystrophy of Francois, Dermoids of cornea, dermoodontodysplasia, diffuse panbronchiolitis, diffuse scleroderma, diffuse systemic sclerosis, Maculopapular Rash due to Ebola virus disease or other diseases or medical conditions, Epidermoid carcinoma, Epidermolysa bullosa simplex and limb girdle muscular dystrophy, Epidermolysis bullosa, Epidermolysis bullosa acquisita, Epidermolysis bullosa herpetiformis, Dowling-Meara, Epidermolysis bullosa intraepidermic, Epidermolysis bullosa letalis, Epidermolysis bullosa simplex, Epidermolysis bullosa simplex with mottled pigmentation, Epidermolysis bullosa simplex, Cockayne-Touraine type, Epidermolysis bullosa simplex, Koebner type, Epidermolysis bullosa simplex, Ogna type, Epidermolysis bullosa with pyloric atresia, Epidermolysis bullosa, dermolytic, Epidermolysis bullosa, generalized atrophic benign, Epidermolysis bullosa, junctional, Epidermolysis bullosa, junctional, with pyloric atrophy, Epidermolysis bullosa, late-onset localized junctional, with mental retardation, Epidermolysis bullosa, lethal acantholytic, Epidermolysis bullosa, pretibial, Epithelial-myoepithelial carcinoma, Epithelioid sarcoma, Epitheliopathy, acute posterior multifocal placoid pigment, Epstein Barr virus, chronic, Erythema elevatum diutinum, Erythema multiform, Erythema nodosum, familial, Erythema nodosum, idiopathic, Erythroblastopenia, Erythroderma desquamativa of Leiner, Erythroderma lethal congenital, Erythrokeratodermia ataxia, Erythrokeratodermia progressive symmetrica ichthyosis, Erythrokeratodermia symmetrica progressive, Erythrokeratodermia variabilis ichthyosis, Erythrokeratodermia variabilis, Mendes da Costa type, Erythrokeratodermia with ataxia, Erythropoietic protoporphyria, Fanconi ichthyosis dysmorphis, Genital herpes, Genital warts, Glutathionuria, Guttate psoriasis, Heat Rash, Herpes simplex encephalitis, Herpes simplex virus 1 & 2, Herpes virus antenatal infection, Herpes zoster ophthalmicus, Herpes zoster oticus, Herpetic keratitis, Ichthyosis, Ichthyosiform erythroderma, Ichthyosis bullosa of Siemens, Ichthyosis cheek eyebrow syndrome, Ichthyosis congenita biliary atresia, Ichthyosis follicularis atrichia photophobia syndrome, Ichthyosis prematurity syndrome, Ichthyosis vulgaris, Ichthyosis, acquired, Ichthyosis, erythrokeratolysis hemalis, Ichthyosis, follicular, Ichthyosis, leukocyte vacuoles, alopecia, and sclerosing cholangitis, Juvenile dermatomyositis, Juvenile macular degeneration and hypotrichosis, Juvenile retinoschisis, Juvenile Scleroderma, Keratosis, seborrheic, Malaria (mosquito bites), Measles, Mumps, Neonatal herpes, Retinis pigmentosa deafness hypogenitalism, Retinitis pigmentosa (various forms), Sjogren's syndrome, Warts, Xeroderma pigmentosum (various forms) and X-linked ichthyosis As specific embodiments, the compounds shown in Formulas I through Formula IV following are included as active and/or efficacy contributing ingredients in the inventive formulation singularly or in combinations.

Formula I:

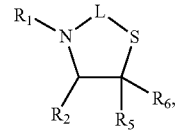

I wherein L is $CR^{t5}R^{t6}$, carbonyl, thiocarbonyl; $R^{t5}$ and $R^{t6}$ are independently H, substituted or unsubstituted alkyl, or substituted or unsubstituted aryl. $R^1$ is H, alkyl, aryl, acyl, $CO_2R^{t3}$, $CONR^3R^4$, $SOR^3$, $SO_2R^3$; $R^2$ is substituted or unsubstituted alkyl, or substituted or unsubstituted aryl, acyl, $CO_2R^{t3}$, $CONR^3R^4$; $R^{t3}$ is H, substituted or unsubstituted alkyl, substituted or unsubstituted aryl, monovalent, divalent or trivalent cation, or a protonated amine; $R^3$ and $R^4$ are independently in multiple occurrences taken from the group H, substituted or unsubstituted, alkyl, substituted or unsubstituted, aryl; $R^5$ and $R^6$ are independently H, substituted or unsubstituted alkyl, or substituted or unsubstituted aryl. In particular L can represent a carbon atom from a sugar such as ribose, glucose. Thus analogs of I include those derived from the condensation of a sugar and the corresponding aminothiol. Examples of such analogs are Glu-cyst and rib-cyst, derived from glucose and ribose respectively.

Formula II:

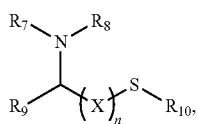

wherein $R^7$ and $R^8$ are independently H, substituted or unsubstituted alkyl, substituted or unsubstituted alkyl aryl, or acyl; $R^9$ is H, substituted or unsubstituted alkyl substituted or unsubstituted aryl, acyl, $CO_2R^{t3}$, $CONR^3R^4$ as set forth for Formula (I); $R^{t3}$ is H, substituted or unsubstituted alkyl, substituted or unsubstituted aryl, monovalent, divalent or trivalent cation, or a protonated amine; X is $CR^5R^6$ wherein $R^5$ and $R^6$ are as defined for Formula I; n=1, 2; and $R^{10}$ is H or acyl.

Formula III:

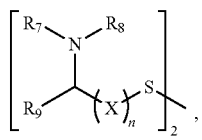

wherein the substituents are as defined for Formula II.

Formula IV:

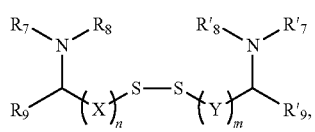

wherein $R^7$, $R^{t7}$, $R^{t8}$ and $R^8$ are independently H, substituted or unsubstituted alkyl, substituted or unsubstituted aryl, acyl; $R^9$ and $R^{t9}$ are independently H, substituted or unsubstituted alkyl, substituted or unsubstituted aryl, acyl, $CO_2R^{t3}$, $CONR^3R^4$; $R^{t3}$ is H, substituted or unsubstituted alkyl, substituted or unsubstituted aryl, monovalent, divalent or trivalent cation, or a protonated amine; X and Y are independently $CR^5R^6$ wherein $R^5$ and $R^6$ are as defined previously for Formula I; n and m are independent and can be either 1 or 2.

The disclosed formulation can contain a single compound or multiple compounds disclosed herein and can also include other compounds know in the art to possess an antibacterial, antiviral (e.g., docosanol), antifungal, analgesic, anesthetic, antiacne, antiyeast, antidandruff, antidermitis, antipuritic, antihistaminic, antiemetic, antimotion sickness, anti-inflammatory, antiperspirant, antiseborric and antipsoriatic activity. In addition the inventive formulation may also contain other compound/s such as those used for hair treatment (shampoos and conditioners), vitamins, retinoids, corticosteroids, sunblocking and sunscreening agents, tanning, The inventive formulation may also be comprised of other agents known to help in the formulation of cosmetics and/or drugs such as benzyl alcohol, butoxydiglycol, butoxyethanol, butoxypropanol, butyl acetate, butanol, butyloctanol, carbomer homopolymer Type C, cetyl alcohol, cocoyl caprylocaprate, cyclodextrins (alpha, beta and gamma), hydroxypropyl beta-cyclodextrin, cycloethoxymethicone, cyclohexane, cyclomethicone, dibutyl adipate, diisobutyl adipate, diisopropyl adipate, diisopropyl oxalate, diisopropyl sebacate, dimethicone, dimethoxydiglycol, dimethyl adipate, dimethyl glutarate, dioctyl adipate, dioctyl sebacate, dioctyl succinate, dipropyl adipate, dipropylene glycol, ethoxydiglycol, ethoxyethanol, 2-ethyl-1,3-hexanediol, isododecane, isooctane, isoparaffin, isopropyl acetate, isopropanol, isopropyl myristate, isopropyl palmitate, methicone, octadecane, octanol, octyl benzoate, oleyl alcohol, oleyl lactate, PEGs (various) including PEG-60, propylene glycol, phenyl methicone, n-propanol, ethyl acetoacetate, methyl acetoacetate, polyoxl 20 cetostearyl ether, propyl acetoacetate, isopropyl acetoacetate, simethicone, stearyl alcohol, bees wax, caprylic/capric triglyceride, castor oil, ceteth-10, ceteth-20, cetyl alcohol, cetyl esters wax, cholesterol, cocamidopropyl betaine, diisopropyl adipate, dimethyl isosorbide, emulsifying wax, ethyl oleate, ethylhexyl hydroxystearate, glyceryl isostearate, glyceryl monostearate, glyceral oleate, isoceteth-20, isopropyl isostearate, isopropyl myristate, isopropyl palmitate, isostearic Acid, isostearyl Alcohol, lanolin Alcohols, laureth-23, laureth-4, modified Lanolin (including medical grade), oleic acid, oleth-10, oleth-20, oleth-5, oleyl alcohol, oleyl oleate, olive oil, peanut oil, PEG 25 propylene glycol stearate, PEG 75 lanolin, poloxamer 124, poloxamer 181, poloxomer 182, poloxamer 188, poloxamer 237, poloxomer 407, polyethylene glycol 300, polyethylene glycol 400, polyethylene glycol 600, PEG Stearate, polyoxyl 20 cetostearyl ether, polyoxyl 40 hydrogenated castor oil, polyoxyl 8 stearate, polysorbate 20, polysorbate 40, polysorbate 60, polysorbate 80, PPG 15 stearyl ether, safflower oil, sodium lauroyl sarcosinate, sorbitan monolaurate, sorbitan monooleate, sorbitan monostearate, sorbitan sesquioleate, sorbitan monopalmitate, soybean oil, squalene, steareth-10, stearate-100, steareth-2, steareth-20, steareth-21, stearyl alcohol, sucrose distearate and silicone oil and other acceptable excipients not limited to those stated above.

The disclosed formulation can contain one or more natural product compound or a compound or compounds from a natural product extract in addition to the compounds disclosed herein. Representative examples of such natural products are for example but not limited to those described as Berberine (all counter ion salt forms), *Echinacea* (*Echinacea angustifolia, Echinacea atrorubens, Echinacea laevigata, Echinacea pallida, Echinacea paradoxa, Echinacea purpurea, Echinacea sanguinea, Echinacea simulata, Echinacea tennesseensis*), Fever Few, lamiaceae e.g., *Thymus vulgaris*, lemongrass oil, sweet basil extract, plantain extract (*plantago major*), rosemary, caffeic acid, *salvia offinalis* extract, swertia chirata extract, lorice, goldenseal extract (hydrastis *canadensis*), Chinese skull cap, Elder, Houttuynia, isatic, lomatium, propolis extract, cajeput oil, tea tree oil, *Calendula officinalis* extract, gum benzoin tincture, albizzia *lebbeck* extract containing saponins, belamcanda *chinensis* extract containing tectorigenin, bisabolol and the like.

The formulation can further contain one or more skin protectant agents as defined in the FDA OTC monograph, § 310.545(a)(18) in addition to the aforementioned compounds and those disclosed herein.

The formulation can further contain skin penetrating agent or agents. Choice of such agent is are those that do not interfere with the overall efficacy of the disclosed formulation.

The inventive formulation can further contain a suitable perfume or perfumes. Choice of such agent/s is/are those that do not interfere with the overall efficacy of the select formulation.

In embodiments, the formulation comprises a suitable sweetener or sweetening agent such as tagatose, saccharin, honey, Stevia (*Stevia* glycosides, *Stevia rebaudiana* extract, *Stevia phebophylia* extract, robus chingis extract), truvia or the like. Choice of such agent/s is/are those that do not interfere with the overall efficacy of the select formulation.

An important challenge is to develop formulations suitable for topical applications that are stable with adequate shelf life and contain NAC or derivatives thereof with ascorbic acid and other active or inactive ingredients that do not compromise the efficacy and use of the formulation for the targeted medical indication/s.

In embodiments, a kit is provided herein including a first container including NAC in powder form and a second container including a non-aqueous liquid carrier, such as glycerol, sorbitol, mannitol, erythritol, xylitol, glyceryl triacetate, propylene glycol, a polyethylene glycol, a polymeric polyol, 1.3-propanediol or a plant extract. In embodiments, the non-aqueous liquid carrier is glycerol. In embodiments, the first container may be substantially free of oxygen gas. In embodiments, the first container includes an inert gas such as argon or nitrogen (e.g. nitrogen). In embodiments, the second container is anhydrous. Prior to administration, the contents of the first container and second contained may be combined to form a formulation or composition provided herein.

In embodiments the first container includes an antioxidant as disclosed herein. Alternatively, the second container contains an antioxidant as disclosed herein. The second container may further include a pH adjuster as known in the art.

The kit provided herein may further include a dispensing apparatus designed to fit onto the first container or the second container after combining in order to dispense the formulation or composition to a subject according to the methods provided herein. In embodiments, the dispensing apparatus is an airless pump (as described above).

Experimental Section

Abbreviations.

Anhyd.: anhydrous; PEG: polyethyleneglycol; IPM: isopropyl myristate; NAC: N-acetyl-L-cysteine; AA: ascorbic acid; PG: propylene glycol; BAC: benzalkonium chloride; MAL: malic acid; MA: maleic acid; GA: glutamic acid; SA: succinic acid; LA: lactic acid.

General.

The base formulation e.g., glycerin, anhydrous glycerin and the like, can be degassed to remove deleterious oxygen by one of the following general techniques: bubbling an inert gas such as nitrogen or argon; heating at 50 to 70° C. under an inert gas atmosphere; subjecting the base formulation to high vacuum; adding an appropriate amount of a chemical degassing agent such as sodium sulfite or ammonium sulfite under an inert atmosphere; and/or sonication under an inert gas atmosphere.

Regardless of the process used for degassing, in embodiments the base formulation may be stirred vigorously where degassing is performed. The residual level of oxygen can be tested by using an oxygen sensing probe. Base formulations that are very viscous could be heated to enable degassing and processing.

Example 1—Formulation 1

100 mL (126 g) of degassed anhydrous glycerin contained in a two necked round bottom flask was stirred under an inert gas (nitrogen) using a magnetic stir bar, and to it was added 0.1 g of powdered ascorbic acid (AA). The mixture was stirred with heating by means of an external hot water bath maintained between 50 to 65° C. to facilitate dissolution of AA if needed. To the warm solution at ~65° C. under nitrogen was added (portion wise) 3 g of powdered N-acetyl cysteine (NAC) and stirring continued until dissolution of NAC is complete. The stirred solution was then cooled to room temperature. This solution was then transferred to airless pumps for dispensing of the finished Formulation 1.

Airless pumps are filled carefully to minimize any headspace and further precaution taken to ensure that capping is performed under a blanket of inert gas to ensure minimal exposure of the formulation to air.

The molar ratio of NAC to AA is 32.28:1.

In a similar manner air backless tubes are filled and the loading end of the tube sealed with a thermal impact sealer.

Example 1-1

The above formulation contained in either an airless tube or pump was then dispensed unto the finger tip of a volunteer with cold sore and applied to the cold sore with a rubbing action to ensure uniform application. The following observations were noted. Pain subsided almost immediately, e.g., in about 1 hour or less. Tingly sensation disappeared within 2-3 hours or sooner and in some instances in less than 1 hour. There was no scar tissue formed with healing. Total healing was completed by 3-7 days of repeated treatment as described above. The formulation was applied every hour during the day time. The treatment was well tolerated with most of the volunteers eager to continue treatment upon completion of the first two applications.

Example 1-2

A male patient with genital herpes lesions was treated with Formulation 1 every 3 hours. Pain subsided within about 1 hour. Tingling sensation disappeared within about 2 hours of application. Healing commenced within 4 hours of application, occurred without any scar tissue being formed and healing occurred in 3 days of repeated treatment.

Example 1-3

A female volunteer presenting with shingles in 5 different spots on her body was treated with 'Formulation 1' twice a day for 2 days. The volunteer had earlier tried a variety of OTC as well as prescription based remedies without success and had given up on those therapies. Pain subsided within one hour of application. Tingly sensation disappeared within one hour of application. Healing was observed within 24 hours without any scar tissue. Complete healing occurred within 2 days of repeated treatment.

Example 2—Formulation 2

Preparation of base formulation for Formulation 2. 190 proof ethanol (15 mL), water 5 mL, glycerin (45 mL) and propylene glycol (10 mL) were mixed with stirring under a blanket of nitrogen gas and heated by placing the mixture in a hot water bath at 70-75° C. LUTROL® L44 (BASF) (10 mL) was then added and stirring continued for 15 minutes. To this mixture was then add PEG4000 (5 g) portion wise with heating until all the PEG4000 is dissolved. Most air bubbles also seem to be expelled at this time. To ensure complete degassing of the mixture it was then degassed by bubbling nitrogen gas through the stirred mixture at room temperature for 15 minutes. At which point the resulting base formulation was stored under a head space of nitrogen in a tightly closed container. This base formulation appeared to be moderately viscous.

Preparation of Formulation 2. 10 g of the above base formulation is transferred to a clean vessel equipped with a suitable magnetic stir bar capable of agitating a viscous mixture and held under a blanket of nitrogen gas. To this base formulation at RT was added 0.1 g of methyl cellulose (Sigma Aldrich) and the mixture stirrer vigorously for 15 minutes. The mixture was then placed in a 65° C. hot water bath and stirring continued. After half hour PEG6000 (1 g) was added and heating with vigorous stirring continued. To this mixture was added 0.11 g of powdered ascorbic acid (AA) and stirring continued for 15 minutes at which point an add mixture of NAC (0.327 g) and 0.221 g [(magnesium stearate (2 portions) and micronized silica (1 portion with respect to magnesium stearate)] were added to the stirred mixture and the results stirred for half hour at 65° C. followed by stirring at RT for 45 minutes.

Once at RT the stirred formulation was degassed with nitrogen for 15 minutes. The resulting creamy white formulation was transferred to two 5 mL air backless pumps and the resulting air tight containers stored at RT for a prolonged period (>2 years).

Smell testing of the formulation after more than 720 days of storage at ambient temperature showed no signs of deterioration as judge by the absence of a distinct sulfurous odor.

The Formulation 2 contains 2.91% NAC on a w/w basis to the total weight of the formulation excluding the weight of AA. AA is present on a 0.97% w/w basis to the total weight of the formulation excluding the weight of NAC. The molar ratio of NAC to AA is 3.22:1.

The admixture of magnesium stearate and micronized silica used in Formulations 2 can vary from 10:1 to 1:1 on a w/w basis.

Example 3—Formulation 3

Preparation of base Formulation 3. Preparation of base Formulation 3 follows: Mix anhydrous glycerin (70 mL; 88.2 g) and distilled or deionized water (23 mL; 23 g) with stirring in a hot water bath at 60° C. To this solution was added LUTROL® 127 (10 g) and isopropyl myristate (2 mL; 1.7 g) and the resulting mixture stirred for 15 minutes after which the temperature of the water bath was increased to 80° C. followed by the addition of PEG4000 (4.5 g) and PEG8000 (4.5 g). The resulting base formulation was gradually cooled to RT with stirring while degassing with nitrogen for 25 minutes. The base formulation was then stored at RT under a blanket of nitrogen.

Preparation of Formulation 3: The above base formulation was reheated by placing it in a hot water bath at 60° C. and was stirred with a magnetic stirrer under a blanket of nitrogen gas. To the stirred base formulation was added ascorbic acid (0.295 g) and stirring continued for 20 minutes. Then NAC (2.32 g) was added together with an add mixture comprised of 0.87 g [(magnesium stearate (~2 portions) and micronized silica (~1 portion with respect to magnesium stearate)] and the resulting formulation stirred at 60° C. for 30 minutes and cooled to RT.

Once at RT the stirred formulation was degassed with nitrogen for 15 minutes. The resulting white formulation was then transferred to appropriate dispensing air tight containers such as air backless tubes. The molar ratio of NAC to AA is 8.515:1.

Formulation 3 was effective for treatment of HSV-1 orofacial infection.

The admixture of magnesium stearate and micronized silica used in Formulations 2 can vary from 10:1 to 1:1 on a w/w basis.

Example 4—Formulation 4

Following the general procedure outlined for Formulation 1, 0.136 g benzalkonium chloride was added first to 100 mL (126 g) of degassed glycerin, followed by 0.5 g of powdered ascorbic acid and 3 g of powdered NAC. The resulting solution was transferred to air backless pumps for dispensing. The molar ratio of NAC to AA is 6.57:1.

Example 4-1

The formulation was effective in the treatment of canker sore. Healing occurred in less than 3 days.

Example 5—Further Formulations

Analytical Methods
Analysis of N-Acetyl Cysteine (NAC).
The existing HPLC USP method for analysis of NAC was modified and utilized for monitoring the stability of NAC in various formulations. Appropriate internal standard (L-phenylalanine) and suitability standard for NAC were employed in HPLC assay.

Analysis of Benzalkonium Chloride (BAC).
The existing HPLC USP method for analysis of BAC was employed. Appropriate suitability standard for BAC was employed in HPLC assay.

Preparation of 1.5 N NaOH in Glycerol.
To anhydrous glycerin (200 mL) is added NaOH (12.036 g) in pellet form or as a ground powder. The mixture is stirred vigorously with gentle heating if needed. If heated caution should be used since the dissolution occurs the reaction is exothermic. Thus the heat source should be turned off at this time. Alternatively, NaOH can be added to cold glycerol which requires powerful mechanical agitation to help dissolution. The homogeneous solution is cooled if heated and degassed with argon or nitrogen gas at ambient temperature before use.

Preparation of CARBOPOL® Ultrez 30 in Glycerin.

Approximately 18 g of anhydrous glycerin contained in small beaker was stirred under an inert gas (nitrogen) using a heavy magnetic stir bar and nitrogen gas is bubbled in through for degassing. After 15 minutes of degassing with nitrogen for removal of oxygen the dissolved oxygen level was checked to ensure that it is below 1 mg/L using a calibrated and clean dissolved oxygen (DO) probe. With continuous flow of nitrogen 0.4 g of powdered Ascorbic Acid (AA) was added to the stirred glycerin. The mixture was stirred at ambient temperature for 20 minutes while degassing. To this solution under nitrogen degassing, 0.6 g of N-acetyl cysteine (NAC) was added portion wise and with vigorous stirring until dissolution of NAC was complete. The solution pH is then adjusted using degassed 1.5N NaOH solution in glycerin. Preparation of this solution was described previously. The pH was adjusted to 4.49 after which 0.2 g of Allantoin was added and stirring with degassing continued. The resulting solution was sonicated for ~5 minutes in a medium powered sonicator (or alternatively could be subjected to gentle vacuum) in order to release any trapped nitrogen bubbles. To the resulting solution was then added 0.2 g of CARBOPOL® Ultrez 30 was added (i.e., sprinkled in) in portions while the solution was stirred at a medium RPM, without degassing but under a blanket of nitrogen until a homogeneous mixture was obtained. The pH of the solution was then readjusted using 1.5N NaOH in anhydrous glycerin to 4.52. Stirring is continued throughout this process under a blanket of nitrogen and 0.2 g of boric acid was added to the solution. The final pH was adjusted using 1.5N in anhydrous glycerin to 4.50.

Airless Pumps with CARBOPOL® Ultrez 30.

Appropriate airless pumps or tubes can be filled with the formulation and capped with the dispensing cap. For the duration of filling the formulation can be kept under continuous nitrogen flow. It is observed that to minimize adjusted pH, several times boric acid can be added prior to of just after the addition of CARBOPOL® Ultrez 30 or just before the addition of CARBOPOL® Ultrez 30. The final formulation prepared can be 2.7% in NAC on a w/w basis.

Formulations.

In each of the formulations 1302-DG through 1306-DG the alternate antioxidant was used in the same millimolar concentration as Ascorbic acid that was used in the first formulation 1300-DG (2.84 mmol/100 g). Anhydrous glycerin was degassed with nitrogen for 15 minutes. The Dissolved Oxygen (DO) level was assessed immediately after degassing and prior to initiation of the filling operation. For all the DG (degassed) formulations the DO level remained below 1 mg/L. Although, the dissolution of ascorbic acid was performed at higher temperatures, dissolution can also be achieved at lower temperatures (e.g., ≤50° C.) so long as powdered or micronized AA is utilized.

Materials Used for the Formulations 1300-DG Through 1306-DG.

Material employed in formulations 1300-DG through 1306-DG are tabulated in Table 1 following.

TABLE 1

| Ingredient | Grade |
|---|---|
| Anhydrous Glycerin | Meets USP testing specifications |
| N-Acetyl-L-Cysteine | USP HD TE |
| Benzalkonium chloride | Meets USP testing specifications |
| Ascorbic Acid | ≥99.0% (HPLC) |

TABLE 1-continued

| Ingredient | Grade |
|---|---|
| Caffeic Acid | ≥98.0% (HPLC) |
| Glutamic Acid | PharmaGrade, EP |
| Succinic Acid | Matrix substance for MALDI-MS, ≥99.5% |
| Malic Acid | Meets USP/NF testing specifications |
| Lactic Acid | Meets USP testing specifications |

Example 5.1—Formulations with NAC, BAC, with and without AA, in Glycerin and without pH Adjustment The following formulations were prepared and evaluated under 3 different ICH conditions via a protocol driven stability study.

Formulation Protocol for 1300-DG.

192.72 g of anhydrous glycerin contained in a three necked round bottom flask was stirred under an inert gas (nitrogen) using a magnetic stir bar and nitrogen gas is bubbled in through for degassing. After 15 minutes of degassing with nitrogen for removal of oxygen the dissolved oxygen level was checked to ensure that it is below 1 mg/L using a calibrated and clean VWR dissolved oxygen (DO) meter. With continuous flow of nitrogen 1.00 g of powdered Ascorbic Acid (AA) was added to the stirred glycerin. The mixture was stirred with heating by means of an external hot water bath maintained between 50 to 65° C. to facilitate dissolution of AA. To the warm solution at ~65° C. under nitrogen 6.06 g of N-acetyl cysteine (NAC) was added portion wise and with stirring until dissolution of NAC was complete. Following the dissolution of NAC, benzalkonium chloride (0.285 g) was added and stirring continued until a homogeneous mixture was obtained. The stirred solution was then cooled to room temperature by removal of a the hot water bath and DO level assessed to ensure that the DO levels are ≤1 mg/L. Throughout the process nitrogen was bubbled through the mixture. Appropriate airless pumps were then filled with the formulation via a peristaltic pump and capped with the dispensing cap. For the duration of filling the formulation is kept under continuous nitrogen flow.

Formulation Protocol for 1301-DG (No Anti-Oxidant).

193.73 g of anhydrous glycerin contained in a three necked round bottom flask was stirred under an inert gas (nitrogen) using a magnetic stir bar and nitrogen gas was bubbled in through for degassing. After 15 minutes of degassing with nitrogen for removal of oxygen the dissolved oxygen level was checked to ensure that it is below 1 mg/L using a calibrated and clean VWR dissolved oxygen (DO) meter. With continuous flow of nitrogen 6.06 g of N-acetyl cysteine (NAC) was added portion wise to the stirred anhydrous glycerin. Heat applied as needed (50-65° C. water bath). Following the dissolution of NAC, benzalkonium chloride (0.285 g) was added and stirring continued until a homogeneous mixture was obtained. The stirred solution was then cooled to room temperature by removal of a the hot water bath and DO level assessed to ensure that the DO levels are ≤1 mg/L. Throughout the process nitrogen was bubbled through the mixture. Appropriate airless pumps were then filled with the formulation via a peristaltic pump and capped with the dispensing cap. For the duration of filling the formulation was kept under continuous nitrogen flow.

Table 2 following tabulates formulations 1300-DG and 1301-DG.

TABLE 2

| Formulation | Key Ingredients | Antioxidant Used | % Label Claim | | |
|---|---|---|---|---|---|
| | | | 25° C. | 30° C. | 40° C. |
| 1300-DG | NAC, BAC, Glycerin | AA | 65.69 | 53.93 | 26.42 |
| 1301-DG | NAC, BAC, Glycerin | No AA | 72.13 | 53.66 | 15.14 |

Example 5.2—Formulations with NAC, AA, in Glycerin and without/with BAC & with No pH Adjustment The following formulation was prepared and evaluated for stability at 25° C. This formulation was prepared analogously to 1300-DG without the addition of BAC.

TABLE 3

| Formulation NGP-1002-(A). | | | | | |
|---|---|---|---|---|---|
| Ingredient | M.W | mmoles | Targeted w/w % | Amount added | Comments/Notes |
| Anhydrous Degassed Glycerin | | | | ~12 g | |
| Powdered Ascorbic Acid | 176.12 | 0.426 | 0.5 | 0.1 g | Heat in water bath (50 to 60° C.) to help dissolution. Degas while stirring. |
| Powdered NAC | 163.195 | 3.68 | 3 | 0.6 g | Degas while stirring at ambient temperature. |
| q.s. with anhydrous Glycerin | | | | | |
| Total Anhydrous Degassed Glycerin added | | | | 16.511 g | |
| Final weight of formulation | | | | 17.211 g | |
| w/w % of NAC | | | | 3.486% | |

TABLE 4

| Formulation NGP-0413. | | | | | |
|---|---|---|---|---|---|
| Ingredient | M.W | mmoles | Targeted w/w % | Amount added | Comments/Notes |
| Anhydrous Degassed Glycerin | | | | 49.871 g | |
| Powdered NAC | 163.195 | 4.59 | 3 | 1.496 g | Degas while stirring at ambient temperature. |
| Powdered AA | | | 0.5 | 0.25 g | Degas while stirring at ambient temperature. |
| Fumed Silica | | | 2.83 | 0.391 g + 1.069 g | Under nitrogen add 1$^{st}$ portion with formulation in water bath at ~60° C. with stirring. Cool to ambient temperature with vigorous stirring while degassing. |

TABLE 4-continued

Formulation NGP-0413.

| Ingredient | M.W | mmoles | Targeted w/w % | Amount added | Comments/Notes |
|---|---|---|---|---|---|
| Final weight of formulation | | | | 51.617 g | |
| w/w % of NAC | | | | 2.89% | |

TABLE 5

Comparison of Formulations NGP-1002-(A), NGP-0413 and NGP-0414.

| | | | % Label Claim | | |
|---|---|---|---|---|---|
| Formulation | Key Ingredients | Antioxidant Used | 25° C. | 30° C. | 40° C. |
| NGP-1002-(A) | NAC, Glycerin | AA | 91 (1 month) | ND | ND |
| NGP-0413 | NAC, Glycerin, fumed SiO$_2$ | AA | ≥60 (214 days) | ND | ND |
| NGP-0414 | NAC, BAC, Glycerin, micronized SiO$_2$ | AA | ≥80 (30 days) | ND | ND |

Example 5.3—Formulations with NAC, BAC, without AA, in Glycerin with Alternate Antioxidants and without pH Adjustment The following formulations were prepared and evaluated under 3 different ICH conditions via a protocol driven stability study.

Formulation Protocol for 1302-DG.

168.94 g of anhydrous glycerin contained in a three necked round bottom flask was stirred under an inert gas (nitrogen) using a magnetic stir bar and nitrogen gas was bubbled in through for degassing. After 15 minutes of degassing with nitrogen for removal of oxygen the dissolved oxygen level was checked to ensure that it is below 1 mg/L using a calibrated and clean VWR dissolved oxygen (DO) meter. With continuous flow of nitrogen 0.928 g of powdered Caffeic Acid was added to the stirred glycerin. The mixture was stirred with heating by means of an external hot water bath maintained between 50 to 65° C. to facilitate dissolution of Caffeic Acid. To the warm solution at ~65° C. under nitrogen 5.315 g of N-acetyl cysteine (NAC) was added portion wise and with stirring until dissolution of NAC was complete. Following the dissolution of NAC, benzalkonium chloride (0.250 g) was added and stirring continued until a homogeneous mixture was obtained. The stirred solution was then cooled to room temperature by removal of a the hot water bath and DO level assessed to ensure that the DO levels are ≤1 mg/L. Throughout the process nitrogen was bubbled through the mixture. Appropriate airless pumps were filled with the formulation via a peristaltic pump and capped with the dispensing cap. For the duration of filling the formulation was kept under continuous nitrogen flow.

Formulation Protocol for 1303-DG.

192.89 g of anhydrous glycerin contained in a three necked round bottom flask was stirred under an inert gas (nitrogen) using a magnetic stir bar and nitrogen gas was bubbled in through for degassing. After 15 minutes of degassing with nitrogen for removal of oxygen the dissolved oxygen level was checked to ensure that it is below 1 mg/L using a calibrated and clean VWR dissolved oxygen (DO) meter. With continuous flow of nitrogen 0.76 g of powdered Malic Acid was added to the stirred glycerin. The mixture was stirred with heating by means of an external hot water bath maintained between 50 to 65° C. to facilitate dissolution. To the warm solution at ~65° C. under nitrogen 6.06 g of N-acetyl cysteine (NAC) was added portion wise and with stirring until dissolution of NAC was complete. Following the dissolution of NAC, benzalkonium chloride (0.285 g) was added and stirring continued until a homogeneous mixture was obtained. The stirred solution was then cooled to room temperature by removal of a the hot water bath and DO level assessed to ensure that the DO levels are ≤1 mg/L. Throughout the process nitrogen is bubbled through the mixture. Appropriate airless pumps were filled with the formulation via a peristaltic pump and capped with the dispensing cap. For the duration of filling the formulation was kept under continuous nitrogen flow.

Formulation Protocol for 1304-DG.

192.82 g of anhydrous glycerin contained in a three necked round bottom flask is stirred under an inert gas (nitrogen) using a magnetic stir bar and nitrogen gas was bubbled in through for degassing. After 15 minutes of degassing with nitrogen for removal of oxygen the dissolved oxygen level is checked to ensure that it is below 1 mg/L using a calibrated and clean VWR dissolved oxygen (DO) meter. With continuous flow of nitrogen 0.76 g of powdered Glutamic Acid was added to the stirred glycerin. The mixture was stirred with heating by means of an external hot water bath maintained between 50 to 65° C. to facilitate dissolution. To the warm solution at ~65° C. under nitrogen 6.06 g of N-acetyl cysteine (NAC) was added portion wise and with stirring until dissolution of NAC is complete. Following the dissolution of NAC, benzalkonium chloride (0.285 g) was added and stirring continued until a homogeneous mixture was obtained. The stirred solution was then cooled to room temperature by removal of a the hot water bath and DO level assessed to ensure that the DO levels are ≤1 mg/L. Throughout the process nitrogen was bubbled through the mixture. Appropriate airless pumps were then filled with the formulation via a peristaltic pump and capped with the dispensing cap. For the duration of filling the formulation was kept under continuous nitrogen flow.

Formulation Protocol for 1305-DG.

192.98 g of anhydrous glycerin contained in a three necked round bottom flask was stirred under an inert gas (nitrogen) using a magnetic stir bar and nitrogen gas is bubbled in through for degassing. After 15 minutes of degassing with nitrogen for removal of oxygen the dissolved oxygen level is checked to ensure that it is below 1 mg/L using a calibrated and clean VWR dissolved oxygen (DO) meter. With continuous flow of nitrogen 0.67 g of powdered Succinic Acid was added to the stirred glycerin. The mixture was stirred with heating by means of an external hot water bath maintained between 50 to 65° C. to facilitate dissolution. To the warm solution at ~65° C. under nitrogen 6.06 g of N-acetyl cysteine (NAC) was added portion wise and with stirring until dissolution of NAC is complete. Following the dissolution of NAC, benzalkonium chloride (0.285 g) was added and stirring continued until a homogeneous mixture was obtained. The stirred solution was then cooled to room temperature by removal of a the hot water bath and DO level assessed to ensure that the DO levels are ≤1 mg/L. Throughout the process nitrogen was bubbled through the mixture. Appropriate airless pumps were then filled with the formulation via a peristaltic pump and capped with the dispensing cap. For the duration of filling the formulation was kept under continuous nitrogen flow.

Formulation Protocol for 1306-DG.

193.02 g of anhydrous glycerin contained in a three necked round bottom flask is stirred under an inert gas (nitrogen) using a magnetic stir bar and nitrogen gas was bubbled in through for degassing. After 15 minutes of degassing with nitrogen for removal of oxygen the dissolved oxygen level is checked to ensure that it is below 1 mg/L using a calibrated and clean VWR dissolved oxygen (DO) meter. With continuous flow of nitrogen 0.54 mL of Lactic Acid (0.63 g*1.209 g/mL) was added to the stirred glycerin. 6.06 g of N-acetyl cysteine (NAC) was added portion wise and with stirring until dissolution of NAC was complete. The mixture was stirred with heating by means of an external hot water bath maintained between 50 to 65° C. to facilitate dissolution. Following the dissolution of NAC, benzalkonium chloride (0.285 g) was added and stirring continued until a homogeneous mixture was obtained. The stirred solution was then cooled to room temperature by removal of a the hot water bath and DO level assessed to ensure that the DO levels are ≤1 mg/L. Throughout the process nitrogen was bubbled through the mixture. Appropriate airless pumps were then filled with the formulation via a peristaltic pump and capped with the dispensing cap. For the duration of filling the formulation was kept under continuous nitrogen flow.

A tabulation of formulations 1303-DG, 1304-DG, 1305-DG and 1306-DG is set forth in Table 6 following.

TABLE 6

Formulations 1303-DG, 1304-DG, 1305-DG and 1306-DG.

| | | | % Label Claim | | |
| --- | --- | --- | --- | --- | --- |
| Formulation | Key Ingredients | Antioxidant Used | 25° C. | 30° C. | 40° C. |
| 1303 DG | NAC, BAC, Glycerin | Malic Acid | 65.54 | 50.37 | 24.06 |
| 1304 DG | NAC, BAC, Glycerin | Glutamic Acid | 66.64 | 54.48 | 25.80 |
| 1305 DG | NAC, BAC, Glycerin | Succinic Acid | 65.09 | 51.86 | 23.57 |
| 1306 DG | NAC, BAC, Glycerin | Lactic Acid | 68.69 | 56.64 | 23.41 |

Formulations set forth in Example 5.4 to 5.7 following were prepared in an analogous manner to those described before. Each Table provides detail of the ingredients used in their respective order of addition. The Table at the end of each Section provides the respective stability results for each set of formulations within the Section. For the results provided below stability testing was conducted at 30° C. and/or 25° C. temperatures.

Example 5.4—Formulations with NAC, AA, BAC, Glycerin, with and without Additional Excipients with pH Adjustment (30° C. Data)

pH 3-4.

Data at pH 3 to pH 4 for formulations NGP-0908-A, NGP-0908-B and NGP-1215 follows:

TABLE 7

Formulation NGP-0908-A.

| Ingredient | M.W | mmoles | Targeted w/w % | Amount added | Comments/Notes |
| --- | --- | --- | --- | --- | --- |
| Anhydrous Degassed Glycerin | | | | ~12 g | |

TABLE 7-continued

Formulation NGP-0908-A.

| Ingredient | M.W | mmoles | Targeted w/w % | Amount added | Comments/Notes |
|---|---|---|---|---|---|
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |
| Aq. NaOH/HCl | Final pH = 3.6 | | | | With stirring at Ambient temperature while degassing. |
| BAC | | | 0.136 | 0.020 g | With stirring at Ambient temperature while degassing. |
| q.s. with anhydrous Glycerin | | | | | |
| Total Anhydrous Degassed Glycerin added | | | | 14.302 g | |
| Final weight of formulation | | | | 15.002 g | |
| w/w % of NAC | | | | 2.97% | |

TABLE 8

Formulation NGP-0908-B.

| Ingredient | M.W | mmoles | Targeted w/w % | Amount added | Comments/Notes |
|---|---|---|---|---|---|
| Anhydrous Degassed Glycerin | | | | ~12 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |
| Aq. NaOH/HCl/ phosphate-citrate buffer | Final pH = ~3.61 | | | | With stirring at Ambient temperature while degassing. |
| BAC | | | 0.136 | 0.020 g | With stirring at Ambient temperature while degassing. |
| q.s. with anhydrous Glycerin | | | | | |
| Total Anhydrous Degassed Glycerin added | | | | 14.206 g | |
| Final weight of formulation | | | | 15.022 g | |
| w/w % of NAC | | | | 2.97% | |

TABLE 9

Formulation NGP-1215.

| Ingredient | M.W | mmoles | Targeted w/w % | Amount added | Comments/Notes |
|---|---|---|---|---|---|
| Anhydrous Degassed Glycerin | | | | 13.1 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |
| Aq. NaOH/HCl/ phosphate-citrate buffer | Final pH = ~3.2 | | | | With stirring at Ambient temperature while degassing. |
| BAC | | 0.136 | | 0.022 g | With stirring at Ambient temperature while degassing. |
| q.s. with anhydrous Glycerin | | | | | |
| Total Anhydrous Degassed Glycerin added | | | | 14.955 g | |
| Final weight of formulation | | | | 15.000 g | |
| w/w % of NAC | | | | 3.00% | |

A comparison of formulations NGP-0908-A, NGP-0908-B and NGP-1215 is set forth in Table 10 following.

TABLE 10

| Formulation | pH | % Label at 30° C./~1 month |
|---|---|---|
| NGP-0908-A | 3.6 | ≥90 |
| NGP-0908-B | 3.7 | ≥90 |
| NGP-1215 | 3.2 | ≥85 | pH 4-5.

Data at pH 4 to pH 5 for formulations NGP-0906-4.5, NGP-0906-b, NGP-0909-A, and NGP-0909-B follows.

TABLE 11

Formulation NGP-0906-4.5.

| Ingredient | M.W | mmoles | Targeted w/w % | Amount added | Comments/Notes |
|---|---|---|---|---|---|
| Anhydrous Degassed Glycerin | | | | ~7.8 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |
| Aq. NaOH/HCl | Final pH = 4.5 | | | | With stirring at Ambient temperature while degassing. |

TABLE 11-continued

Formulation NGP-0906-4.5.

| Ingredient | M.W | mmoles | Targeted w/w % | Amount added | Comments/Notes |
|---|---|---|---|---|---|
| BAC | | | 0.136 | 0.020 g | With stirring at Ambient temperature while degassing. |
| q.s. with anhydrous Glycerin | | | | | |
| Total Anhydrous Degassed Glycerin added | | | | 14.181 g | |
| Final weight of formulation | | | | 15.012 g | |
| w/w % of NAC | | | | 2.97% | |

TABLE 12

Formulation NGP-0906-b.

| Ingredient | M.W | mmoles | Targeted w/w % | Amount added | Comments/Notes |
|---|---|---|---|---|---|
| Anhydrous Degassed Glycerin | | | | ~7.8 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |
| Aq. NaOH/HCl/ Sodium acetate | Final pH = 4.58 | | | | With stirring at Ambient temperature while degassing. |
| BAC | | | 0.136 | 0.020 g | With stirring at Ambient temperature while degassing. |
| q.s. with anhydrous Glycerin | | | | | |
| Total Anhydrous Degassed Glycerin added | | | | 13.681 g | |
| Final weight of formulation | | | | 15.012 g | |
| w/w % of NAC | | | | 2.97% | |

TABLE 13

Formulation NGP-0909-A.

| Ingredient | M.W | mmoles | Targeted w/w % | Amount added | Comments/Notes |
|---|---|---|---|---|---|
| Anhydrous Degassed Glycerin | | | | ~7.8 g | |
| Powdered Ascorbic Acid | 176.12 | 0.426 | 0.5 | 0.075 g | Heat in water bath (50 to 60° C.) to help dissolution. Degas while stirring. |

TABLE 13-continued

Formulation NGP-0909-A.

| Ingredient | M.W | mmoles | Targeted w/w % | Amount added | Comments/Notes |
|---|---|---|---|---|---|
| Powdered NAC | 163.195 | 3.68 | 3 | 0.45 g | Degas while stirring at ambient temperature. |
| Aq. NaOH/HCl | Final pH = 4.58 | | | | With stirring at Ambient temperature while degassing. |
| BAC | | | 0.136 | 0.021 g | With stirring at Ambient temperature while degassing. |
| q.s. with anhydrous Glycerin | | | | | |
| Total Anhydrous Degassed Glycerin added | | | | 13.381 g | |
| Final weight of formulation | | | | 15.002 g | |
| w/w % of NAC | | | | 2.97% | |

TABLE 14

Formulation NGP-0909-B.

| Ingredient | M.W | mmoles | Targeted w/w % | Amount added | Comments/Notes |
|---|---|---|---|---|---|
| Anhydrous Degassed Glycerin | | | | ~7.8 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |
| Aq. NaOH/HCl/ phosphate-citric acid | Final pH = 4.58 | | | | With stirring at Ambient temperature while degassing. |
| BAC | | | 0.136 | 0.021 g | With stirring at Ambient temperature while degassing. |
| q.s. with anhydrous Glycerin | | | | | |
| Total Anhydrous Degassed Glycerin added | | | | 13.681 g | |
| Final weight of formulation | | | | 15.002 g | |
| w/w % of NAC | | | | 2.97% | |

A comparison of formulations NGP-0906-4.5, NGP-0906-b, NGP-0909-A, and NGP-0909-B is set forth in Table 15 following.

TABLE 15

| Formulation | pH | % Label at 30° C./~1 month |
|---|---|---|
| NGP-906-4.5 | 4.5 | ≥90 |
| NGP-0906-b | 4.58 | ≥90 |
| NGP-0909-A | 4.6 | ≥80 |
| NGP-0909-B | 4.61 | ≥70 (99 days) | pH 5-6.

Data at pH 5 to pH 6 for formulations NGP-0104-2 and NGP-0104-4 follows.

TABLE 16

Formulation NGP-0104-2.

| Ingredient | M.W | mmoles | Targeted w/w % | Amount added | Comments/Notes |
|---|---|---|---|---|---|
| Anhydrous Degassed Glycerin | | | | ~16.5 g | |
| Powdered NAC | 163.195 | 4.59 | 3 | 0.75 g | Degas while stirring at ambient temperature. |
| BAC | | | ~0.136 | 0.027 g | |
| Aq. NaOH/HCl | Adjusted pH = 5.55 | | | | With stirring at Ambient temperature while degassing. |
| Powdered AA | | | 0.5 | 0.1 | |
| Aq. NaOH/HCl | Adjusted pH = 5.55 from 5.09 post addition of AA | | | | With stirring at Ambient temperature while degassing. |
| q.s. with anhydrous Glycerin | | | | | |
| Total Anhydrous Degassed Glycerin added | | | | 18.26 g | |
| Final weight of formulation | | | | 20.019 g | |
| w/w % of NAC | | | | 3.75% | |

TABLE 17

Formulation NGP-0104-4.

| Ingredient | M.W | mmoles | Targeted w/w % | Amount added | Comments/Notes |
|---|---|---|---|---|---|
| Anhydrous Degassed Glycerin | | | | ~16.5 g | |
| Powdered NAC | 163.195 | 4.59 | 3 | 0.75 g | Degas while stirring at ambient temperature. |
| BAC | | | ~0.136 | 0.027 g | |
| Aq. NaOH/HCl | Adjusted pH = 5.59 | | | | With stirring at Ambient temperature while degassing. |
| Powdered AA | | | 0.5 | 0.1 | |
| Aq. NaOH/HCl | Adjusted pH = 5.55 from 5.09 post addition of AA | | | | With stirring at Ambient temperature while degassing. |

TABLE 17-continued

Formulation NGP-0104-4.

| Ingredient | M.W | mmoles | Targeted w/w % | Amount added | Comments/Notes |
|---|---|---|---|---|---|
| CARBOPOL ® Ultrez 30 | | | 0.1895 | 0.076 g | With vigorous stirring at Ambient temperature while degassing. |
| q.s. with anhydrous Glycerin | | | | | |
| Total Anhydrous Degassed Glycerin added | | | | 18.184 g | |
| Final weight of formulation | | | | 20.090 g | |
| w/w % of NAC | | | | 2.97% | |

A comparison of formulations NGP-0104-2 and NGP-0104-4 is set forth in Table 18 following.

TABLE 18

| Formulation | pH | % Label at 30° C./14 days |
|---|---|---|
| NGP-0104-2 | 5.55 | ≥90 |
| NGP-0104-4 | 5.55 | ≥90 | pH 6-7.

Data at pH 6 to pH 7 for formulations NGP-0828-4 and NGP-0910-B follow.

TABLE 19

Formulation NGP-0828-4.

| Ingredient | M.W | mmoles | Targeted w/w % | Amount added | Comments/Notes |
|---|---|---|---|---|---|
| Anhydrous Degassed Glycerin | | | | ~16 g | |
| BAC | NA | NA | 0.136 | 0.028 g | |
| Powdered Ascorbic Acid | 176.12 | 0.57 | 0.5 | 0.1 g | Heat in water bath (50 to 60° C.) to help dissolution. Degas while stirring. |
| Powdered NAC | 163.195 | 3.68 | 3 | 0.6 g | Degas while stirring at ambient temperature. |
| Aq. NaOH/HCl | Final pH = 6.77 | | | | With stirring at Ambient temperature while degassing. |
| q.s. with anhydrous Glycerin | | | | | |
| Total Anhydrous Degassed Glycerin added | | | | 19.373 g | |
| Final weight of formulation | | | | 20.017 g | |
| w/w % of NAC | | | | 2.99% | |

TABLE 20

Formulation NGP-0910-B.

| Ingredient | M.W | mmoles | Targeted w/w % | Amount added | Comments/Notes |
|---|---|---|---|---|---|
| Anhydrous Degassed Glycerin | | | | ~6 g | |
| Powdered Ascorbic Acid | 176.12 | 0.426 | 0.5 | 0.15 g | Heat in water bath (50 to 60° C.) to help dissolution. Degas while stirring. |
| Powdered NAC | 163.195 | 3.68 | 3 | 0.9 g | Degas while stirring at ambient temperature. |
| Aq. NaOH/HCl/ phosphate-citric acid | Final pH = 6.78 | | | | With stirring at Ambient temperature while degassing. |
| BAC | | | 0.136 | 0.042 g | With stirring at Ambient temperature while degassing. |
| q.s. with anhydrous Glycerin | | | | | |
| Total Anhydrous Degassed Glycerin added | | | | 23.161 g | |
| Final weight of formulation | | | | 30.025 g | |
| w/w % of NAC | | | | 2.99% | |

A comparison of formulations NGP-0828-4 and NGP-0910-B is set forth in Table 21 following.

TABLE 21

| Formulation | pH | % Label at 30° C./~1 month | Comments |
|---|---|---|---|
| NGP-0828-4 | 6.73 | ≥70 (55 days) | BAC added at first to Glycerin. |
| NGP-0910-B | 6.78 | ≥90 | BAC added last post AA, NAC and pH adjustment. |

Example 5.5—Formulations with NAC, AA, BAC, Glycerin, with Additional Excipients and/or Antioxidants with pH Adjustment (30° C. Data)

Formulations NGP-1221, NGP-1228 and NGP-1228-B are set forth in the following tables.

TABLE 22

Formulation NGP-1221.

| Ingredient | M.W | mmoles | Targeted w/w % | Amount added | Comments/Notes |
|---|---|---|---|---|---|
| Anhydrous Degassed Glycerin | | | | 13.193 g | |
| Powdered Ascorbic Acid | 176.12 | 0.426 | 0.5 | 0.100 g | Heat in water bath (50 to 60° C.) to help dissolution. Degas while stirring. |
| Ascorbyl Palmitate | 414.53 | 0.03 | 0.06 | 0.012 g | Degas while stirring at ambient temperature. |
| Lactic acid | 90.08 | 0.667 | (85% w/w aqueous) | 0.06 g | Degas while stirring at ambient temperature. |
| Glutamic acid | 147.13 | 0.564 | 0.02 | 0.083 g | Degas while stirring at ambient temperature. |

TABLE 22-continued

Formulation NGP-1221.

| Ingredient | M.W | mmoles | Targeted w/w % | Amount added | Comments/Notes |
|---|---|---|---|---|---|
| Lipoic acid | 206.32 | 0.111 | 0.114 | 0.023 g | Degas while stirring at ambient temperature. |
| Mannitol | 182.172 | 1.22 | 0.99 | 0.2 g | Degas while stirring at ambient temperature. |
| Powdered NAC | 163.195 | 3.68 | 3 | 0.6 g | Degas while stirring at ambient temperature. |
| Aq. NaOH/HCl/ phosphate-citrate buffer | Final pH = 3.51 | | | | With stirring at Ambient temperature while degassing. |
| BAC | | | ~0.136 | 0.027 g | With stirring at Ambient temperature while degassing. |
| q.s. with anhydrous Glycerin | | | | | |
| Total Anhydrous Degassed Glycerin added | | | | 18.266 g | |
| Final weight of formulation | | | | 20.171 g | |
| w/w % of NAC | | | | 2.974% | |

TABLE 23

Formulation NGP-1228.

| Ingredient | M.W | mmoles | Targeted w/w % | Amount added | Comments/Notes |
|---|---|---|---|---|---|
| Sorbitan Monooleate | | | 7 | 0.7 g | |
| Sorbitan Sesquioleate | | | 2 | 0.2 g | |
| Anhydrous Degassed Glycerin | | | | 6.312 g | |
| Powdered Ascorbic Acid | 176.12 | 0.426 | 0.5 | 0.05 g | Heat in water bath (50 to 60° C.) to help dissolution. Degas while stirring. |
| Lipoic acid | 206.32 | | 0.109 | 0.011 g | Degas while stirring at ambient temperature. |
| Ascorbyl Palmitate | 414.53 | | 0.06 | 0.006 g | Degas while stirring at ambient temperature. |
| Mannitol | 182.172 | | 0.55 | 0.100 g | Degas while stirring at ambient temperature. |
| Powdered NAC | 163.195 | 3.68 | 3 | 0.3 g | Degas while stirring at ambient temperature. |
| 1.5N NaOH in anhydrous glycerin | Final pH = 3.57 | | | | With stirring at Ambient temperature while degassing. |

TABLE 23-continued

Formulation NGP-1228.

| Ingredient | M.W | mmoles | Targeted w/w % | Amount added | Comments/Notes |
|---|---|---|---|---|---|
| BAC | | | ~0.136 | 0.013 g | With stirring at Ambient temperature while degassing. |
| q.s. with anhydrous Glycerin | | | | | |
| Total Anhydrous Degassed Glycerin added | | | | 8.545 g | |
| Final weight of formulation | | | | 10.096 g | |
| w/w % of NAC | | | | 2.97% | |

TABLE 24

Formulation NGP-1228-B.

| Ingredient | M.W | mmoles | Targeted w/w % | Amount added | Comments/Notes |
|---|---|---|---|---|---|
| Sorbitan Monooleate | | | 7 | 0.7 g | |
| Sorbitan Sesquioleate | | | 2 | 0.2 g | |
| Anhydrous Degassed Glycerin | | | | 6.312 g | Degassing continued after adding to sorbitan excipient derivatives while stirring at ambient temperature. |
| Powdered Ascorbic Acid | 176.12 | 0.426 | 0.5 | 0.05 g | Heat in water bath (50 to 60° C.) to help dissolution. Degas while stirring. |
| Lipoic acid | 206.32 | | 0.109 | 0.011 g | Degas while stirring at ambient temperature. |
| Ascorbyl Palmitate | 414.53 | | 0.06 | 0.006 g | Degas while stirring at ambient temperature. |
| Mannitol | 182.172 | | 0.55 | 0.100 g | Degas while stirring at ambient temperature. |
| Powdered NAC | 163.195 | 3.68 | 3 | 0.3 g | Degas while stirring at ambient temperature. |
| 1.5N NaOH in anhydrous glycerin/ phosphate-citrate buffer | Final pH = 3.59 | | | | With stirring at Ambient temperature while degassing. |
| BAC | | | ~0.136 | 0.013 g | With stirring at Ambient temperature while degassing. |
| q.s. with anhydrous Glycerin | | | | | |
| Total Anhydrous Degassed Glycerin added | | | | 8.106 g | |
| Final weight of formulation | | | | 10.010 g | |
| w/w % of NAC | | | | 2.99% | |

A comparison of formulations NGP-1221, NGP-1228 and NGP-1228-B is set forth in Table 25 following.

TABLE 25

| Formulation | pH | % Label at 30° C./~15 days |
|---|---|---|
| NGP-1221 | 3.6 | ≥90 |
| NGP-1228 | 3.57 | ≥90 |
| NGP-1228-B | 3.59 | ≥90 |

Example 5.6—Formulations of NAC, AA, Glycerin, with or without Additional Excipients with pH Adjustment (30° C. Data)

Formulations NGP-0828-2, NGP-0912-A, NGP-0912-B, NGP-1107-b and NGP-1108 are set forth in the following tables.

TABLE 26

Formulation NGP-0828-2.

| Ingredient | M.W | mmoles | Targeted w/w % | Amount added | Comments/Notes |
|---|---|---|---|---|---|
| Anhydrous Degassed Glycerin | | | | ~17 g | |
| Powdered Ascorbic Acid | 176.12 | 0.57 | 0.5 | 0.1 g | Heat in water bath (50 to 60° C.) to help dissolution. Degas while stirring. |
| Powdered NAC | 163.195 | 3.68 | 3 | 0.6 g | Degas while stirring at ambient temperature. |
| Aq. NaOH/HCl | Final pH = 6.77 | | | | With stirring at Ambient temperature while degassing. |
| q.s. with anhydrous Glycerin | | | | | |
| Total Anhydrous Degassed Glycerin added | | | | 18.514 g | |
| Final weight of formulation | | | | 20.017 g | |
| w/w % of NAC | | | | 2.99% | |

TABLE 27

Formulation NGP-0912-A.

| Ingredient | M.W | mmoles | Targeted w/w % | Amount added | Comments/Notes |
|---|---|---|---|---|---|
| Anhydrous Degassed Glycerin | | | | ~6.8 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |

TABLE 27-continued

Formulation NGP-0912-A.

| Ingredient | M.W | mmoles | Targeted w/w % | Amount added | Comments/Notes |
|---|---|---|---|---|---|
| Aq. NaOH/HCl q.s. with anhydrous Glycerin | Final pH = 5.54 | | | | With stirring at Ambient temperature while degassing. |
| Total Anhydrous Degassed Glycerin added | | | | 14.115 g | |
| Final weight of formulation | | | | 15.155 g | |
| w/w % of NAC | | | | 2.97% | |

TABLE 28

Formulation NGP-0912-B.

| Ingredient | M.W | mmoles | Targeted w/w % | Amount added | Comments/Notes |
|---|---|---|---|---|---|
| Anhydrous Degassed Glycerin | | | | ~6.8 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.45 g | Degas while stirring at ambient temperature. |
| Aq. NaOH/HCl/ phosphate-citrate buffer q.s. with anhydrous Glycerin | Final pH = 5.55 | | | | With stirring at Ambient temperature while degassing. |
| Total Anhydrous Degassed Glycerin added | | | | 13.965 g | |
| Final weight of formulation | | | | 15.155 g | |
| w/w % of NAC | | | | 2.97% | |

TABLE 29

Formulation NGP-1107-b.

| Ingredient | M.W | mmoles | Targeted w/w % | Amount added | Comments/Notes |
|---|---|---|---|---|---|
| Anhydrous Degassed Glycerin:PEG300:PEG400:PEG600 | | | | 16.889 g | 40:5:49:0.76 w/w ratio respectively. All PEGs contain BHT |
| Powdered Ascorbic Acid | 176.12 | 0.426 | 0.5 | 0.1 g | Heat in water bath (50 to 60° C.) to help dissolution. Degas while stirring. |

TABLE 29-continued

Formulation NGP-1107-b.

| Ingredient | M.W | mmoles | Targeted w/w % | Amount added | Comments/Notes |
|---|---|---|---|---|---|
| Powdered NAC | 163.195 | 3.68 | 3 | 0.602 g | Degas while stirring at ambient temperature. |
| Aq. NaOH/HCl/phosphate-citrate buffer | Final pH = 3.56 | | | | With stirring at Ambient temperature while degassing. |
| q.s. with Anhydrous Degassed Glycerin | | | | 1.567 g | |
| Final weight of formulation | | | | 20.003 g | |
| w/w % of NAC | | | | 3.01% | |

TABLE 30

Formulation NGP-1108.

| Ingredient | M.W | mmoles | Targeted w/w % | Amount added | Comments/Notes |
|---|---|---|---|---|---|
| Anhydrous Degassed Glycerin | | | | 12.034 g | |
| GLUCAM™ P20 | | | | 0.762 g | |
| Powdered Ascorbic Acid | 176.12 | 0.426 | 0.5 | 0.075 g | Heat in water bath (50 to 60° C.) to help dissolution. Degas while stirring. |
| Powdered NAC | 163.195 | 3.68 | 3 | 0.450 g | Degas while stirring at ambient temperature. |
| Aq. NaOH/HCl | Final pH = 3.00 | | | | With stirring at Ambient temperature while degassing. |
| q.s. with Anhydrous Degassed Glycerin | | | | | |
| Final weight of formulation | | | | 15.093 g | |
| w/w % of NAC | | | | 2.98% | |

A comparison of formulations NGP-0828-2, NGP-0912-A, NGP-0912-B, NGP-1107-b and NGP-1108 is set forth in Table 31 following.

TABLE 31

| Formulation | pH | % Label at 30° C./~1 month |
|---|---|---|
| NGP-0828-2 | 6.77 | ≥90 |
| NGP-0912-A | 5.54 | ≥80 (91 days) |
| NGP-0912-B | 5.55 | ≥90 |
| NGP-1107-b | 3.63 | ≥80 |
| NGP-1108 | 3.00 | ≥80 |

Example 5.7—Formulations with NAC, Glycerin, and Additional Excipient/s with pH Adjustment (30° C. Data)

Formulations NGP-1108-A and NGP-1108-B, are set forth in the following tables.

TABLE 32

Formulation NGP-1108-A.

| Ingredient | M.W | mmoles | Targeted w/w % | Amount added | Comments/Notes |
|---|---|---|---|---|---|
| Anhydrous Degassed Glycerin | | | | ~9.013 g | |
| Powdered NAC | 163.195 | 3.68 | 3 | 0.9 g | Degas while stirring at ambient temperature. |
| Aq. NaOH/HCl | Final pH = 4.59 | | | | With stirring at Ambient temperature while degassing. Best to remove trapped gas bubbles with slight vacuum or sonication before proceeding to the next step. |
| CARBOPOL ® Ultrez 30 | | | 0.1895 | 0.078 g | With vigorous stirring at Ambient temperature under nitrogen blanket. |
| q.s. with anhydrous Glycerin | | | | | |
| Total Anhydrous Degassed Glycerin added | | | | 9.433 g | |
| Final weight of formulation | | | | 10.078 g | |
| w/w % of NAC | | | | 2.97% | |

TABLE 33

Formulation NGP-1108-B.

| Ingredient | M.W | mmoles | Targeted w/w % | Amount added | Comments/Notes |
|---|---|---|---|---|---|
| Anhydrous Degassed Glycerin | | | | ~9.013 g | |
| Powdered NAC | 163.195 | 3.68 | 3 | 0.9 g | Degas while stirring at ambient temperature. |
| Aq. NaOH/HCl/ phosphate-citrate buffer | Final pH = 4.59 | | | | With stirring at Ambient temperature while degassing. Best to remove trapped gas bubbles with slight vacuum or sonication before proceeding to the next step. |
| CARBOPOL ® Ultrez 30 | | | 0.1895 | 0.078 g | With vigorous stirring at Ambient temperature under nitrogen blanket. |
| q.s. with anhydrous Glycerin | | | | | |
| Total Anhydrous Degassed Glycerin added | | | | 9.880 g | |
| Final weight of formulation | | | | 10.18 g | |
| w/w % of NAC | | | | 2.95% | |

A comparison of formulations NGP-1108-A and NGP-11087-B is set forth in Table 34 following.

TABLE 34

| Formulation | pH | % Label at 30° C./~1 month |
|---|---|---|
| NGP-1108-A | 4.59 | |
| NGP-1108-B | 4.59 | ≥85 (50 days) |

EMBODIMENTS

Embodiments disclosed herein include Embodiments P1 to P37 following.

Embodiment P1

A pharmaceutical composition comprising a pharmaceutical acceptable carrier, an N-acetylcysteine or derivative thereof and an amount of an antioxidant compound sufficient to reduce oxidation of said N-acetylcysteine or derivative thereof relative to the absence of said antioxidant.

Embodiment P2

The pharmaceutical composition of embodiment P1, wherein said pharmaceutical composition is a liquid or semi-solid composition.

Embodiment P3

The pharmaceutical composition of embodiment P2, wherein said liquid or semi-solid composition is a lotion, gel, cream or ointment.

Embodiment P4

The pharmaceutical composition of embodiment P1 or P2, wherein said pharmaceutical acceptable carrier is glycerol, sorbitol, mannitol, erythritol, xylitol, glyceryl triacetate, propylene glycol, a polyethylene glycol, a polymeric polyols or a plant extract.

Embodiment P5

The pharmaceutical composition of embodiment P1 or P2, wherein said pharmaceutical acceptable carrier is glycerol.

Embodiment P6

The pharmaceutical composition of any one of embodiments P1 to P5, wherein the antioxidant is acetyl cysteine, ascorbic acid, ascorbic acid polypeptide, ascorbyl dipalmitate, ascorbyl methylsilanol pectinate, ascorbyl palmitate, ascorbyl stearate, betalains (betanin), betaxanthine (e.g., indicaxanthine) BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, vitamin D, quinic acid, chlorogenic acid, glutathione, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate or tris(nonylphenyl)phosphite.

Embodiment P7

The pharmaceutical composition of any one of embodiments P1 to P4, wherein said antioxidant is ascorbic acid.

Embodiment P8

The pharmaceutical composition of embodiment P7, wherein the molar ratio of said N-acetylcysteine to ascorbic acid is in the range from 2200:1 to 2:1.

Embodiment P9

The pharmaceutical composition of any one of embodiments P1 to P8, wherein said amount of said antioxidant is sufficient to reduce oxidation of said N-acetylcysteine or derivative thereof by at least 50%, 60%, 70%, 80%, 90% or 99% relative to the absence of said antioxidant over a period of at least 1, 7, 14, 30, 60, 90, 120, 365 or 730 days at a storage temperature of about 20° C. to 30° C.

Embodiment P10

The pharmaceutical composition of any one of embodiments P1 to P9, wherein said pharmaceutical composition is within a container that is substantially free of oxygen gas.

Embodiment P11

The pharmaceutical composition of embodiment P10, wherein said container comprises an inert gas.

Embodiment P12

The pharmaceutical composition of embodiment P11, wherein said inert gas is nitrogen or argon.

Embodiment P13

The pharmaceutical composition of any one of embodiments P1 to P12, wherein said pharmaceutical composition is a topical pharmaceutical composition.

Embodiment P14

The pharmaceutical composition of any one of embodiments P1 to P13, wherein said N-acetylcysteine or derivative thereof is present at a concentration of about 0.1% w/w to about 20% w/w.

Embodiment P15

The pharmaceutical composition of any one of embodiments P1 to P14, wherein the said N-acetylcysteine or derivative thereof is an N-acetylcysteine salt, N-acetylcysteine ester, N-acetylcysteine amide or N-acetylcysteine metal thiol chelate.

Embodiment P16

The pharmaceutical composition of any one of embodiments P1 to P15, further comprising a silica, silicate, silicic acid, silatrane glycol, metal silicate, alumina or aluminate.

Embodiment P17

The pharmaceutical composition of any one of embodiments P6 to P16, further comprising a gelling agent.

Embodiment P18

The pharmaceutical composition of any one of embodiments P6 to P16 comprising a dental paste.

Embodiment P19

The pharmaceutical composition of any one of embodiments P1 to P18, wherein said pharmaceutical composition is a pharmaceutical composition.

Embodiment P20

An pharmaceutical formulation comprising an N-acetylcysteine or derivative thereof.

Embodiment P21

The pharmaceutical formulation of embodiment P20, further comprising a non-aqueous liquid carrier.

Embodiment P22

The pharmaceutical formulation of embodiment P21, wherein said non-aqueous liquid carrier is glycerol, sorbitol, mannitol, erythritol, xylitol, glyceryl triacetate, propylene glycol, a polyethylene glycol, a polymeric polyols or a plant extract.

Embodiment P23

The pharmaceutical formulation of embodiment P21, wherein said non-aqueous liquid carrier is glycerol.

Embodiment P24

The pharmaceutical formulation of any one of embodiments P20 to P23, wherein said anhydrous pharmaceutical formulation within a container that is substantially free of oxygen gas.

Embodiment P25

The pharmaceutical formulation of any one of embodiments P20 to P24, wherein said container comprises an inert gas.

Embodiment P26

The pharmaceutical formulation of any one of embodiments P20 to P24, wherein said container comprises nitrogen gas or argon gas.

Embodiment P27

The pharmaceutical formulation of any one of embodiments P20 to P26, wherein said pharmaceutical formulation does not comprise an antioxidant.

Embodiment P28

The pharmaceutical formulation of any one of embodiments P20 to P26, wherein said pharmaceutical formulation does not comprise ascorbic acid or derivative thereof.

Embodiment P29

The pharmaceutical formulation of any one of embodiments P20 to P28, wherein said pharmaceutical composition is an anhydrous pharmaceutical composition.

Embodiment P30

A dermal patch comprising an N-acetylcysteine or derivative thereof and an amount of an antioxidant compound sufficient to reduce oxidation of said N-acetylcysteine or derivative thereof relative to the absence of said antioxidant.

Embodiment P31

A method of treating a herpesvirus infection in a subject, said method comprising administering an effective amount of the pharmaceutical composition of one of embodiments 1 to 28 or the dermal patch of embodiment P30.

Embodiment P32

The method of embodiment P31, wherein said administering is topically administering.

Embodiment P33

The method of embodiment P31 or P32, wherein said herpesvirus infection in said subject presents as a cold sore, genital herpes, or shingles.

Embodiment P34

The method of any one of embodiments P31 to P33, wherein said subject present no symptoms of said herpesvirus infection within 2 to 10 days of said administration.

Embodiment P35

A method for preparing a pharmaceutical composition, said method comprising mixing an N-acetylcysteine or derivative thereof with a liquid pharmaceutical carrier within a container, wherein said liquid pharmaceutical carrier is anhydrous and substantially free of oxygen gas.

Embodiment P36

The method of embodiment P35, wherein said vessel contains an inert gas and is sealed from ambient air.

Embodiment P37

The method of embodiment P36, wherein said inert gas is argon or nitrogen.

Additional Embodiments

Additional embodiments of the subject matter disclosed herein include embodiments X1 to X22 following.

Embodiment X1

A topical composition for treating a skin condition comprising N-acetylcysteine or derivative thereof stabilized against oxidation by the use of a suitable sacrificial antioxidant, at least one humectant and/or absorbent and/or a skin protectant agent and/or an astringent and/or absorbent and/or keratolytic agent, wherein the application provides an enhanced rate of relief and healing of the skin condition within 1 to less than 10 days.

Embodiment X2

The topical composition of embodiment X1 for the better relief from and management of chronic skin conditions such as various forms of psoriasis, atopic dermatitis, chemically induced lesions (such as those from chemotherapy) and eczema.

Embodiment X3

The composition for treating a skin condition of embodiment X1 where the skin condition is HSV-1 or HSV-2.

Embodiment X4

A composition for treating a skin condition as in Embodiment X1 where the amino acid derivative are selected from any of Formulae (I) to (IV) disclosed herein or mixtures thereof.

Embodiment X5

A composition for treating a skin condition as in Embodiment X1 where the concentration of the compound from Embodiment X4 is in a range of about 0.1% to 20% of the final formulation.

Embodiment X6

A composition for treating a skin condition as in Embodiment X1 wherein the said humectant/s is/are selected from the group for example such as glycerol, sorbitol, mannitol, erythritol, xylitol, glyceryl triacetate, propylene glycol, PEG (various), and polymeric polyols like polydextrose, or natural extracts like quillaia, lactic acid, or urea.

Embodiment X7

A composition for treating a skin condition as in Embodiment X1 wherein the said compound when and where possible is a salt (organic or inorganic) or ester or amide or metal thiol chelated form.

Embodiment X8

A composition for treating a skin condition as in Embodiment X1 further comprising silica or silicate/s or silicic acid (meta-, di-, pyro- or ortho-silicic acids or organic or inorganic salts thereof or mixtures thereof) or silatrane glycol or metal silicates or alumina or aluminates or mixtures thereof in micronized or non-micronized forms.

Embodiment X9

A composition for treating a skin condition as in Embodiment X1 further comprising an acceptable emulsifier and emulsion stabilizers e.g., sodium hypophosphite.

Embodiment X10

A composition for treating a skin condition as in Embodiment X1 further comprising an acceptable gelling agent such as aloe vera and/or pectin or pectin with a low degree of esterification (meaning less than or equal to 25% esterification) or esterified pectin or pectin amides or other pectin derivatives.

Embodiment X11

A composition for treating a skin condition as in Embodiment X1 further comprising a non-sulfur or sulfur containing sacrificial antioxidant.

Embodiment X12

A composition for treating a skin condition as in Embodiments X11 where the antioxidant/s is/are selected from a group such as acetyl cysteine, ascorbic acid, ascorbic acid polypeptide, ascorbyl dipalmitate, ascorbyl methylsilanol pectinate, ascorbyl palmitate, ascorbyl stearate, betalains (betanin), betaxanthine (e.g., indicaxanthine) BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, vitamin D, quinic acid, chlorogenic acid, glutathione, and tris(nonylphenyl)phosphite, or mixtures thereof.

Embodiment X13

A composition for treating a skin condition as in Embodiment X1 where the skin condition is shingles.

Embodiment X14

A method of dosing to topically treat a skin condition with a formulation of Embodiment 1 wherein the formulation is applied onto the skin every 1 to 2 hours or twice or thrice or four times a day for a period of up to 1-2 to less than 10 days.

Embodiment X15

A method of dosing to topically treat a skin condition as in embodiment X14 wherein the skin condition is one of HSV-1 (cold sore) & 2, PHN, shingles or genital herpes or warts.

Embodiment X16

A method of dosing to topically treat a skin condition with a formulation of Embodiment X1 wherein the dosing is performed with a dermal patch that is applied onto the affected skin.

Embodiment X17

A method of dosing to topically treat a skin condition with a formulation of Embodiment X1 or Embodiment X5 which is suitably adapted to form a lotion, gel, cream, or ointment.

Embodiment X18

A method of dosing to topically treat a skin condition with a formulation of Embodiment X1 or Embodiment X7 which contains an additional therapeutic agent such as antibacterial, antiviral, antifungal, analgesic, anesthetic, antiacne, antiyeast, antidandruff, antidermitis, antipuritic, antihistaminic, antiemetic, antimotion sickness, anti-inflammatory, antiperspirant, antiseborric and antipsoriatic activity.

Embodiment X19

A method of dosing to topically treat a skin condition with a formulation of Embodiment X1 or Embodiment X5 which contains additional compound/s such as those: known for hair treatment (shampoos and conditioners); known as vitamins, retinoids, corticosteroids; for sunblocking and sunscreening and tanning.

Embodiment X20

A method of dosing to topically treat a skin condition with a formulation of Embodiment X19 which is suitably adapted to form a lotion, gel, cream, or ointment.

Embodiment X21

A method of dosing to topically treat a skin condition with a formulation of Embodiment X19 wherein the dosing is performed with a dermal patch that is applied onto the affected skin.

Embodiment X22

A method for dispensing the topical formulation composition in Embodiment X21 via a suitable airless pump or tube.

Further Embodiments

Further embodiments are set forth in embodiments 1 to 40 following.

Embodiment 1

A pharmaceutical composition comprising a pharmaceutical acceptable carrier, an N-acetylcysteine or derivative thereof and antioxidant compound.

Embodiment 2

The pharmaceutical composition of embodiment 1, wherein said pharmaceutical composition is a liquid or semi-solid composition.

Embodiment 3

The pharmaceutical composition of embodiment 1, further comprising a reducing agent.

Embodiment 4

The pharmaceutical composition of embodiment 2, wherein said liquid or semi-solid composition is a lotion, gel, cream or ointment.

Embodiment 5

The pharmaceutical composition of any one of embodiments 1 or 2, wherein said pharmaceutical acceptable carrier is glycerol, sorbitol, mannitol, erythritol, xylitol, glyceryl triacetate, propylene glycol, a polyethylene glycol, a polymeric polyols or a plant extract.

Embodiment 6

The pharmaceutical composition of any one of embodiments 1 or 2, wherein said pharmaceutical acceptable carrier is glycerol.

Embodiment 7

The pharmaceutical composition of embodiment 6, wherein said pharmaceutical acceptable carrier is glycerol mixed with a gelling agent.

Embodiment 8

The pharmaceutical composition of any one of embodiments 1 to 7, wherein the antioxidant is acetyl cysteine, ascorbic acid, ascorbic acid polypeptide, ascorbyl dipalmitate, ascorbyl methylsilanol pectinate, ascorbyl palmitate, ascorbyl stearate, betalains (betanin), betaxanthine (e.g., indicaxanthine) BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, vitamin D, quinic acid, chlorogenic acid, glutathione, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate or tris(nonylphenyl)phosphite.

Embodiment 9

The pharmaceutical composition of any one of embodiments 1 to 5, wherein said antioxidant is ascorbic acid.

Embodiment 10

The pharmaceutical composition of embodiment 9, wherein the molar ratio of said N-acetylcysteine to ascorbic acid is in the range from 2200:1 to 2:1.

Embodiment 11

The pharmaceutical composition of any one of embodiments 1 to 10, wherein said amount of said antioxidant is sufficient to reduce oxidation of said N-acetylcysteine or derivative thereof by at least 50%, 60%, 70%, 80%, 90% or 99% relative to the absence of said antioxidant over a period of at least 1, 7, 14, 30, 60, 90, 120, 365 or 730 days at a storage temperature of about 20° C. to 30° C.

Embodiment 12

The pharmaceutical composition of any one of embodiments 1 to 11, further comprising a pH adjuster, wherein the pH adjuster is NaOH or KOH.

Embodiment 13

The pharmaceutical composition of any one of embodiments 1 to 12, wherein said pharmaceutical composition is within a container that is substantially free of oxygen gas.

Embodiment 14

The pharmaceutical composition of embodiment 13, wherein said container comprises an inert gas.

Embodiment 15

The pharmaceutical composition of embodiment 14, wherein said inert gas is nitrogen or argon.

Embodiment 16

The pharmaceutical composition of any one of embodiments 1 to 15, wherein said pharmaceutical composition is a topical pharmaceutical composition.

Embodiment 17

The pharmaceutical composition of any one of embodiments 1 to 16, wherein said N-acetylcysteine or derivative thereof is present at a concentration of about 0.1% w/w to about 20% w/w.

Embodiment 18

The pharmaceutical composition of any one of embodiments 1 to 16, wherein the said N-acetylcysteine or derivative thereof is an N-acetylcysteine salt, N-acetylcysteine ester, N-acetylcysteine amide or N-acetylcysteine metal thiol chelate.

Embodiment 19

The pharmaceutical composition of any one of embodiments 1 to 18, further comprising a silica, silicate, silicic acid, silatrane glycol, metal silicate, alumina or aluminate.

Embodiment 20

The pharmaceutical composition of any one of embodiments 8 to 19, further comprising a gelling agent.

Embodiment 21

The pharmaceutical composition of any one of embodiments 8 to 19, further comprising a dental paste.

Embodiment 22

The pharmaceutical composition of any one of embodiments 1 to 21, wherein said pharmaceutical composition is a non-aqueous pharmaceutical composition.

Embodiment 23

A pharmaceutical formulation comprising an N-acetylcysteine or derivative thereof.

Embodiment 24

The pharmaceutical formulation of embodiment 23, further comprising a non-aqueous liquid carrier.

Embodiment 25

The pharmaceutical formulation of embodiment 24, wherein said non-aqueous liquid carrier is glycerol, sorbitol, mannitol, erythritol, xylitol, glyceryl triacetate, propylene glycol, a polyethylene glycol, a polymeric polyols or a plant extract.

Embodiment 26

The pharmaceutical formulation of embodiment 24, wherein said non-aqueous liquid carrier is glycerol.

Embodiment 27

The pharmaceutical formulation of any one of embodiments 23 to 26, wherein said anhydrous pharmaceutical formulation is within a container that is substantially free of oxygen gas.

Embodiment 28

The pharmaceutical formulation of any one of embodiments 23 to 27, wherein said container further comprises an inert gas.

Embodiment 29

The pharmaceutical formulation of any one of embodiments 23 to 28, wherein said container further comprises nitrogen gas or argon gas.

Embodiment 30

The pharmaceutical formulation of any one of embodiments 23 to 29, wherein said pharmaceutical formulation does not comprise an antioxidant.

Embodiment 31

The pharmaceutical formulation of any one of embodiments 23 to 29, wherein said pharmaceutical formulation does not comprise ascorbic acid or derivative thereof.

Embodiment 32

The pharmaceutical formulation of any one of embodiments 23 to 31, wherein said pharmaceutical composition is an anhydrous pharmaceutical composition.

Embodiment 33

A dermal patch comprising an N-acetylcysteine or derivative thereof and an amount of an antioxidant compound sufficient to reduce oxidation of said N-acetylcysteine or derivative thereof relative to the absence of said antioxidant.

Embodiment 34

A method of treating a herpesvirus infection in a subject, said method comprising administering to a subject in need thereof an effective amount of the pharmaceutical composition of one of embodiments 1 to 22 or the dermal patch of embodiment 33.

Embodiment 35

The method of embodiment 34, wherein said administering is topically administering.

Embodiment 36

The method of any one of embodiments 34 or 35, wherein said herpesvirus infection in said subject presents as a cold sore, genital herpes, or shingles.

Embodiment 37

The method of any one of embodiments 34 to 36, wherein said subject present no symptoms of said herpesvirus infection within 2 to 10 days of said administration.

Embodiment 38

A method for preparing a pharmaceutical composition, said method comprising mixing an N-acetylcysteine or derivative thereof with a liquid pharmaceutical carrier within a container, wherein said liquid pharmaceutical carrier is anhydrous and substantially free of oxygen gas.

Embodiment 39

The method of embodiment 38, wherein said vessel contains an inert gas and is sealed from ambient air.

Embodiment 40

The method of embodiment 39, wherein said inert gas is argon or nitrogen.

What is claimed is:

1. A topical pharmaceutical composition comprising:
   (i) glycerol;
   (ii) about 0.5 w/w % to about 20 w/w % of N-acetylcysteine;
   (iii) about 0.01 w/w % to about 5.0 w/w % of ascorbic acid; and
   (iv) optionally benzalkonium chloride.

2. The topical pharmaceutical composition of claim 1, comprising:
   (i) glycerol;
   (ii) about 1.0 w/w % to about 10.0 w/w % of N-acetylcysteine;
   (iii) about 0.1 w/w % to about 1.0 w/w % of ascorbic acid; and
   (iv) about 0.10 w/w % to about 0.15 wt/% benzalkonium chloride.

3. The topical pharmaceutical composition of claim 2, comprising:
   (i) glycerol;
   (ii) about 3 w/w % of N-acetylcysteine;
   (iii) about 0.5 w/w % of ascorbic acid; and
   (iv) about 0.13 w/w % benzalkonium chloride.

4. The topical pharmaceutical composition of claim 1, further comprising sodium hydroxide.

5. The topical pharmaceutical composition of claim 1, wherein the topical pharmaceutical composition comprises from 77.1 w/w % to 95.3 w/w % of glycerol.

6. The topical pharmaceutical composition of claim 1, wherein the topical pharmaceutical composition comprises less than 10 w/w % of water.

7. A topical pharmaceutical composition comprising:
   a pharmaceutically acceptable carrier selected from the group consisting of glycerol, sorbitol, mannitol, erythritol, xylitol, glyceryl triacetate, propylene glycol, polyethylene glycol, and a combination of two or more thereof;
   (ii) from about 0.5% w/w to about 20% w/w of N-acetylcysteine, N-acetylhomocysteine, N,N'-diacetylcysteine, an N-acetylcysteine salt, an N-acetylcysteine ester, an N-acetylcysteine amide, or an N-acetylcysteine metal thiol chelate; and
   (iii) an antioxidant selected from the group consisting of caffeic acid, glutamic acid, succinic acid, maleic acid, lactic acid, lipoic acid, ascorbic acid, ascorbyl-2-glucoside, ascorbic acid 2-phosphate, ascorbic acid 2-sulfate, ascorbyl-6-octanoate, ascorbyl laurate, ascorbyl myristate, ascorbyl-6-palmitate, ascorbyl-6-stearate, ascorbyl-2,6-dipalmitate, kojic acid, ferulic acid, alpha-tocopherol, and a combination of two or more thereof.

8. The composition of claim 7, further comprising benzalkonium chloride.

9. The composition of claim 7, further comprising sodium hydroxide, potassium hydroxide, or a combination thereof.

10. The composition of claim 7, further comprising a topical analgesic agent.

11. The composition of claim 7, comprising from about 0.01 w/w % to about 5.0 w/w % of the antioxidant.

12. The composition of claim 7, wherein the non-aqueous pharmaceutically acceptable carrier comprises glycerol.

13. The composition of claim 7, wherein the non-aqueous pharmaceutically acceptable carrier comprises glycerol and sorbitol.

14. The composition of claim 7, wherein the antioxidant is ascorbic acid.

15. The pharmaceutical composition of claim 7, wherein the topical pharmaceutical composition is a liquid composition or a semi-solid composition.

16. The composition of claim 7, further comprising a reducing agent, a gelling agent, or a combination thereof.

17. The composition of claim 7, wherein the antioxidant is selected from the group consisting of ascorbic acid, ascorbyl-2-glucoside, ascorbic acid 2-phosphate, ascorbic acid 2-sulfate, ascorbyl-6-octanoate, ascorbyl laurate, ascorbyl myristate, ascorbyl-6-palmitate, ascorbyl-6-stearate, ascorbyl-2,6-dipalmitate, a mixture of ascorbic acid and kojic acid, a mixture of ascorbic acid and ferulic acid, a mixture of ascorbic acid and alpha-tocopherol, and a combination of two or more thereof.

18. The composition of claim 7, wherein the antioxidant is selected from the group consisting of caffeic acid, glutamic acid, succinic acid, maleic acid, lactic acid, ascorbic acid, and a combination of two or more thereof.

19. The composition of claim 7, further comprising a reducing agent selected from the group consisting of aminoethanesulfinic acid, ammonium sulfate, ammonium thiolactate, ammonium thioglycolate, calcium thioglycolate, cysteine, a cysteine salt, dithioglycolate, magnesium thioglycolate, potassium thioglycolate, sodium thioglycolate, strontium thioglycolate, ethanolamine dithioglycolate, ethanolamine thioglycolate, glyceryl thiopropionate, hydroquinone, lysine HCl, mercaptopropionic acid, thioglycerin, thioglycolic acid, histidine HCl, cysteamine, dihydroxy acetone, stannous chloride, thiomorpholinone, and a combination of two or more thereof.

20. The composition of claim 7, further comprising a gelling agent selected from the group consisting of a cross-linked homopolymer of acrylic acid, a $C_{10-30}$ alkyl acrylate crosspolymer with hydrophobically modified crosslinked polyacrylate polymer, or a combination of thereof.

21. The pharmaceutical composition of claim 7, wherein the pharmaceutical composition comprises less than 10 w/w % of water.

22. The pharmaceutical composition of claim 21, wherein the pharmaceutical composition comprises less than 5 w/w % of water.

23. An anhydrous topical pharmaceutical formulation comprising:

(i) N-acetylcysteine, N-acetylhomocysteine, N,N'-diacetylcysteine, an N-acetylcysteine salt, an N-acetylcysteine ester, an N-acetylcysteine amide, or an N-acetylcysteine metal thiol chelate; and (ii) a non-aqueous liquid carrier selected from the group consisting of glycerol, sorbitol, mannitol, erythritol, xylitol, glyceryl triacetate, propylene glycol, a polyethylene glycol, and a combination of two or more thereof.

24. The anhydrous topical pharmaceutical formulation of claim 23, further comprising an antioxidant.

25. A dermal patch comprising the pharmaceutical composition of claim 1.

26. A dermal patch comprising the pharmaceutical composition of claim 7.

27. A dermal patch comprising the pharmaceutical composition of claim 23.

28. A container comprising: (i) the pharmaceutical composition of claim 1, and (ii) an oxygen scavenger.

29. A container comprising: (i) the pharmaceutical composition of claim 7, and (ii) an oxygen scavenger.

30. A container comprising: (i) the pharmaceutical composition of claim 23, and (ii) an oxygen scavenger.

31. A method of treating a herpesvirus infection, a canker sore, or shingles in a subject in need thereof, said method comprising topically administering to the subject an effective amount of the pharmaceutical composition of claim 1.

32. The method of claim 31, wherein the herpesvirus infection is a cold sore or genital herpes.

33. A method of treating a herpesvirus infection, a canker sore, or shingles in a subject in need thereof, said method comprising topically administering to the subject an effective amount of the pharmaceutical composition of claim 7.

34. The method of claim 33, wherein the herpesvirus infection is a cold sore or genital herpes.

35. A method of treating a herpesvirus infection, a canker sore, or shingles in a subject in need thereof, said method comprising topically administering to the subject an effective amount of the pharmaceutical composition of claim 21.

36. The method of claim 35, wherein the herpesvirus infection is a cold sore or genital herpes.

* * * * *